(12) United States Patent
Oost et al.

(10) Patent No.: US 9,440,930 B2
(45) Date of Patent: *Sep. 13, 2016

(54) SUBSTITUTED BICYCLIC DIHYDROPYRIMIDINONES AND THEIR USE AS INHIBITORS OF NEUTROPHIL ELASTASE ACTIVITY

(71) Applicant: Boehringer Ingelheim International GmbH, Ingelheim am Rhein (DE)

(72) Inventors: Thorsten Oost, Biberach an der Riss (DE); Ralf Anderskewitz, Laupheim (DE); Christian Gnamm, Biberach an der Riss (DE); Gerd Morschhaeuser, Biberach an der Riss (DE); Stefan Peters, Biberach an der Riss (DE); Uwe Joerg Ries, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/809,311

(22) Filed: Jul. 27, 2015

(65) Prior Publication Data

US 2016/0031831 A1 Feb. 4, 2016

(30) Foreign Application Priority Data

Jul. 31, 2014 (EP) .................................. 14179261

(51) Int. Cl.
*C07D 239/82* (2006.01)
*C07D 405/06* (2006.01)
*A61K 31/517* (2006.01)
*C07D 239/70* (2006.01)

(52) U.S. Cl.
CPC .......... *C07D 239/82* (2013.01); *C07D 239/70* (2013.01)

(58) Field of Classification Search
None
See application file for complete search history.

(56) References Cited

U.S. PATENT DOCUMENTS

| | | | |
|---|---|---|---|
| 8,580,800 B2 | 11/2013 | Von Nussbaum et al. | |
| 8,889,700 B2 | 11/2014 | Von Nussbaum et al. | |
| 9,040,516 B2 | 5/2015 | Shiro et al. | |
| 9,115,093 B2 * | 8/2015 | Gnamm ............... | C07D 403/12 |
| 2009/0093477 A1 | 4/2009 | Ray et al. | |
| 2010/0010024 A1 | 1/2010 | Von Nussbaum et al. | |
| 2011/0034433 A1 | 2/2011 | Von Nussbaum et al. | |
| 2012/0004203 A1 | 1/2012 | Von Nussbaum et al. | |
| 2012/0094968 A1 | 4/2012 | Von Nussbaum et al. | |
| 2013/0065913 A1 | 3/2013 | Blench et al. | |
| 2014/0249129 A1 | 9/2014 | Gnamm et al. | |

FOREIGN PATENT DOCUMENTS

| | | |
|---|---|---|
| CA | 2656307 A1 | 1/2008 |
| DE | 102006031314 A1 | 1/2008 |
| DE | 102007061766 A1 | 6/2009 |
| DE | 102009004197 A1 | 7/2010 |
| GB | 2392910 A | 3/2004 |
| WO | 03053930 | 7/2003 |
| WO | 2004020410 A2 | 3/2004 |
| WO | 2004020412 A1 | 3/2004 |
| WO | 2004024700 A1 | 3/2004 |
| WO | 2004024701 A1 | 3/2004 |
| WO | 2005082863 A2 | 9/2005 |

(Continued)

OTHER PUBLICATIONS

International Search Report and Written Opinion for corresponding application, PCT/EP2015/067506, date of mailing Sep. 24, 2015.

(Continued)

*Primary Examiner* — Emily Bernhardt
(74) *Attorney, Agent, or Firm* — Michael P. Morris; Edward S. Lazer

(57) ABSTRACT

Substituted bicyclic dihydropyrimidinones of formula 1

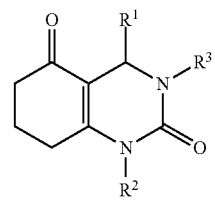

and their use as inhibitors of neutrophil elastase activity. An exemplary compound is

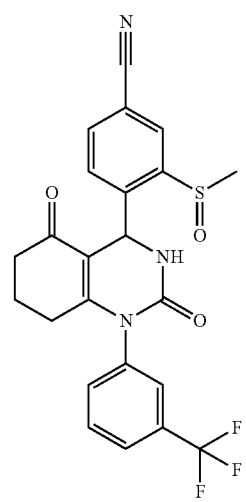

1.a.

8 Claims, No Drawings

(56) References Cited

FOREIGN PATENT DOCUMENTS

| WO | 2005082864 | A1 | 9/2005 |
|---|---|---|---|
| WO | 2006082412 | A2 | 8/2006 |
| WO | 2006136857 | A1 | 12/2006 |
| WO | 2007129060 | A1 | 11/2007 |
| WO | 2008135537 | A1 | 11/2008 |
| WO | 2009013444 | A1 | 1/2009 |
| WO | 2009037413 | A1 | 3/2009 |
| WO | 2009060158 | A1 | 5/2009 |
| WO | 2009060203 | A1 | 5/2009 |
| WO | 2009060206 | A1 | 5/2009 |
| WO | 2009080199 | A1 | 7/2009 |
| WO | 2009135599 | A1 | 11/2009 |
| WO | 2010078953 | A1 | 7/2010 |
| WO | 2010115548 | A1 | 10/2010 |
| WO | 2011110858 | A1 | 9/2011 |
| WO | 2011110859 | A1 | 9/2011 |
| WO | 2012002502 | A1 | 1/2012 |
| WO | 2013018804 | A1 | 2/2013 |
| WO | 2014009425 | A1 | 1/2014 |
| WO | 2014029830 | A1 | 2/2014 |
| WO | 2014029831 | A1 | 2/2014 |
| WO | 2014029832 | A1 | 2/2014 |
| WO | 2014035414 | A1 | 3/2014 |
| WO | 2014122160 | A1 | 8/2014 |
| WO | 2014/134414 | * | 9/2014 |

OTHER PUBLICATIONS

Abstract in English for DE102007061766, Jun. 25, 2009.
Abstract in English for WO2012002502, May 1, 2012.
Sjo et al., "Neutrophil elastase inhibitors: recent advances in the development of mechanism-based and nonelectrophilic inhibitors", Future Medicinal Chemistry, vol. 4, 2012, p. 651-660.

* cited by examiner

SUBSTITUTED BICYCLIC DIHYDROPYRIMIDINONES AND THEIR USE AS INHIBITORS OF NEUTROPHIL ELASTASE ACTIVITY

This invention relates to substituted bicyclic dihydropyrimidinones of formula 1

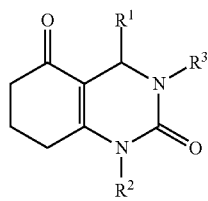

and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other autoimmune and allergic disorders, allograft rejection, and oncological diseases.

BACKGROUND INFORMATION

The following references describe neutrophil elastase inhibitors with a monocyclic dihydro-pyrimidinone core: GB2392910, WO04024700, WO05082864, WO05082863, DE102006031314, US100010024, WO10115548, WO09080199, DE102007061766, WO06136857, WO06082412, WO12002502.

The following references describe neutrophil elastase inhibitors with a bicyclic tetra-hydropyrrolopyrimidinedione core: WO07129060, WO08135537, US090093477, WO09013444, WO09060206, WO09060203, WO09060158, US110034433.

The following references describe neutrophil elastase inhibitors with core structures other than those herein before mentioned: WO04020412, WO04020410, WO03053930, WO10078953, WO09135599, DE102009004197, WO11110858, WO11110859, WO09060158, WO09037413, WO04024701, US130065913, WO13018804, WO12002502, WO2014029831, US 2014/0171414, WO14009425, WO2014029832, WO2014029830, WO14122160 and WO14135414.

For a review on various inhibitors of neutrophil elastase see: P. Sjö (*Future Med. Chem.* 2012, 4, 651-660).

BRIEF SUMMARY OF THE INVENTION

Neutrophil elastase (NE) is a 29 kDa serine protease. It is expressed in bone marrow precursor cells, stored in the granula of peripheral blood granulocytes at high concentrations and it is released upon cellular activation. To the substrates of NE belong major elements of the extracellular matrix (ECM): elastin, fibronectin, laminin, collagen and proteoglycans. Neutrophil elastase activity leads to ECM degradation, increases migration and chemotaxis of monocytes and vascular smooth muscle cells and directly affects components of the coagulation and fibrinolytic pathways (PAI-1 and TFPI). Increased activity of neutrophil elastase is associated with chronic inflammatory and fibrotic diseases of several organs. The potential of neutrophil elastase inhibitors as anti-inflammatory therapies has been reviewed by P. A. Henriksen in *Current Opinion in Hematology* 2014, 21, 23-28 Inhibitors of neutrophil elastase will therefore have an important role for the treatment of different diseases like COPD, idiopathic pulmonary fibrosis and other fibrotic diseases, cancer, acute lung injury, acute respiratory distress syndrome, bronchiectasis, cystic fibrosis, alpha1-antitrypsin deficiency and others.

The problem of the present invention is to prepare new compounds which on the basis of their pharmaceutical effectiveness as inhibitors of neutrophil elastase activity, may be used therapeutically, that is for the treatment of pathophysiological processes caused by increased activity of neutrophil elastase.

It has surprisingly been found that the compounds of the present invention have the following properties which are advantageous in view of the indications of the current invention.

The compounds according to the present invention, including the physiologically acceptable salts, are effective as inhibitors of neutrophil elastase and exhibit favourable inhibitory potency, as determined by the half maximal inhibitory concentration ($IC_{50}$), in an enzymatic inhibition assay.

Some compounds according to the present invention, including the physiologically acceptable salts, are additionally effective as inhibitors of neutrophil serin protease proteinase 3 and exhibit favourable inhibitory potency, as determined by the half maximal inhibitory concentration ($IC_{50}$), in an enzymatic inhibition assay. This inhibitory activity on a second neutrophil serin protease may be beneficial for pharmacological efficacy.

Some compounds according to the present invention, including the physiologically acceptable salts, exhibit favourable inhibitory potency, as determined by the half maximal effective concentration ($EC_{50}$), in a plasma or whole-blood assay, for instance as described in T. Stevens et al. (*J. Pharm. Exp. Ther.* 2011, 339, 313-320).

Some compounds according to the present invention, including the physiologically acceptable salts, exhibit favourable in vivo potency, as determined, for example, by the half maximal effective dose ($ED_{50}$), in models of human neutrophil elastase-induced lung injury in mouse or rat, for instance as described in Tremblay et al. (*Chest* 2002, 121, 582-588) or T. Stevens et al. (*J. Pharm. Exp. Ther.* 2011, 339, 313-320).

Some compounds according to the present invention, including the physiologically acceptable salts, exhibit favourable metabolic stability in an in vitro microsomal assay for metabolic stability as described in E. Kerns & L. Di (*Drug-like properties: concepts, structure design and methods: from ADME to toxicity optimization*, Elsevier, 1$^{st}$ ed, 2008), chapter 29 and references therein.

Some compounds according to the present invention, including the physiologically acceptable salts, exhibit favourable metabolic stability in an in vitro hepatocytes assay for metabolic stability as described in E. Kerns & L. Di (*Drug-like properties: concepts, structure design and methods: from ADME to toxicity optimization*, Elsevier, 1$^{st}$ ed, 2008), chapter 29 and references therein.

An improved metabolic stability in an in vitro test system is expected to translate into a reduced in vivo clearance (CL), because the metabolic conversion in the liver is reduced. Based on the pharmacokinetic equation $CL/F_{oral}=Dose/AUC$ ($F_{oral}$: oral bioavailability, AUC: area under the curve), a reduced in vivo clearance is expected to lead to higher dose-normalized systemic exposure (AUC) of the drug.

Some compounds according to the present invention, including the physiologically acceptable salts, exhibit favourable permeability in an in vitro Caco-2 cell layer method for permeability as described in E. Kerns & L. Di (Drug-like properties: concepts, structure design and methods: from ADME to toxicity optimization, Elsevier, 1$^{st}$ ed, 2008), chapter 26 and references therein. For an oral drug, improved permeability is expected to translate into a higher fraction of the drug absorbed in the intestinal tract, thus, resulting in higher dose-normalized systemic exposure (AUC).

Some compounds according to the present invention, including the physiologically acceptable salts, exhibit a favourable, that is low efflux ratio (permeability in the efflux direction divided by the permeability in the influx direction) in an in vitro Caco-2 or MDCK cell layer method as described in E. Kerns & L. Di (Drug-like properties: concepts, structure design and methods: from ADME to toxicity optimization, Elsevier, 1$^{st}$ ed, 2008), chapter 26 and 27 and references therein. For an oral drug, an improved, that is reduced efflux ratio is expected to translate into a higher fraction of the drug absorbed in the intestinal tract, thus, resulting in higher dose-normalized systemic exposure (AUC).

Some compounds according to the present invention, including the physiologically acceptable salts, exhibit favourable aqueous solubility in a kinetic or thermodynamic solubility method as described in E. Kerns & L. Di (Drug-like properties: concepts, 15 structure design and methods: from ADME to toxicity optimization, Elsevier, 1$^{st}$ ed, 2008), chapter 25 and references therein. For an oral drug, improved aqueous solubility is expected to translate into a higher fraction of the drug absorbed in the intestinal tract resulting in higher dose-normalized systemic exposure (AUC) and/or oral bioavailability ($F_{oral}$) and/or peak plasma concentration after administration ($C_{max}$). Furthermore, improved aqueous solubility is expected to reduce the risk of development challenges, such as expensive formulations, increased development time, high drug load.

Comparatively higher dose-normalized systemic exposure (AUC) can be advantageous in several ways: (1) If a certain systemic exposure (AUC) needs to be achieved for efficacy, the drug can be dosed in a lower amount. Lower dosages have the advantages of lower drug load (parent drug and metabolites thereof) for the patient causing potentially less side effects, and lower production costs for the drug product. (2) Comparatively higher dose-normalized systemic exposure (AUC) can lead to increased efficacy or prolonged duration of action of the drug when the same dose is applied.

Some compounds according to the present invention, including the physiologically acceptable salts, exhibit favourable metabolic stability, favourable permeability and favourable aqueous solubility. Accordingly, some compounds of the present invention are expected to exhibit favourable pharmacokinetic (PK) properties after oral dosing, in particular favourable systemic exposure (area under the curve, AUC), thus, leading to favourable efficacy in vivo.

Some compounds according to the present invention, including the physiologically acceptable salts, exhibit favourable pharmacokinetic (PK) properties. The PK properties can be determined in pre-clinical animal species, for example mouse, rat, hamster, dog, guinea pig, mini pig, cynomolgus monkey, rhesus monkey. The PK properties of a compound can be described, for example, by the following parameters: Mean residence time (MRT), elimination half-live ($t_{1/2}$), volume-of-distribution ($V_D$), area under the curve (AUC), clearance (CL) and bioavailability after oral administration ($F_{oral}$), peak plasma concentration after administration ($C_{max}$), time to reach Cmax ($T_{max}$).

The compounds of the invention and metabolites thereof are devoid of the hydrazine substructure that causes structural alerts for mutagenicity and carcinogenicity as described in Benigni et al. (Chem. Rev. 2011, 11, 2507-2536). Thus, compounds of the invention may bear the advantage of reduced genotoxic potential.

Some compounds according to the present invention, including the physiologically acceptable salts, exhibit favourable, that is low inhibition of cytochrome P450 (CYP) isozymes in corresponding in vitro assays for CYP isozyme inhibition as described in E. Kerns & L. Di (Drug-like properties: concepts, structure design and methods: from ADME to toxicity optimization, Elsevier, 1$^{st}$ ed, 2008), chapter 32 and references therein. Reduced inhibition of CYP isozymes is expected to translate into a reduced risk for undesirable drug-drug interactions which is the interference of one drug with the normal metabolic or pharmacokinetic behaviour of a co-administered drug.

Some compounds according to the present invention, including the physiologically acceptable salts, exhibit favourable, that is low Cytochrome P450 (CYP) induction potential. CYP induction can affect the pharmacokinetics of a drug molecule upon multiple dosing, which can result in pharmacokinetic drug-drug interactions with coadministered drugs. CYP induction can lead to decreased exposure of the inducing compound (e.g. autoinduction) or decreased exposure of a coadministered compound metabolized by the induced enzyme. CYP induction can also lead to an increase in the metabolism of a drug causing changes in pharmacological (active metabolite) and toxicological (toxic metabolite) outcomes.

Some compounds according to the present invention, including the physiologically acceptable salts, exhibit favourable, that is low, inhibition of the hERG channel in a patch clamp assay as described in E. Kerns & L. Di (Drug-like properties: concepts, structure design and methods: from ADME to toxicity optimization, Elsevier, 1$^{st}$ ed, 2008), chapter 34 and references cited therein.

DETAILED DESCRIPTION OF THE INVENTION

1. A compound of formula 1

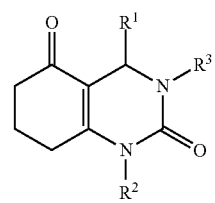

wherein
$R^1$ is phenyl, substituted with CN and
  substituted with a second substituent $R^{1.1}$,
  $R^{1.1}$ is selected from the group consisting of
    —SO$_2$—CH$_3$, —SO—CH$_3$, —CH$_2$—OH, —SO$_2$—CH$_2$CH$_2$—OH, —SO$_2$—CH$_2$CH$_2$—OCH$_3$ and —SO$_2$—CH$_2$CH$_2$CH$_2$—OH $R^2$ is phenyl substituted with $CF_3$
$R^3$ is selected from the group consisting of H, $CH_3$, —CO—NH—$CH_3$, —$CH_2CH_2$—OH and —$CH_2$-oxetane
or optical and geometrical isomers, solvates, hydrates or salts, preferably pharmaceutically acceptable salts, thereof, provided that a compound of formula 1 is not a compound selected from the group consisting of

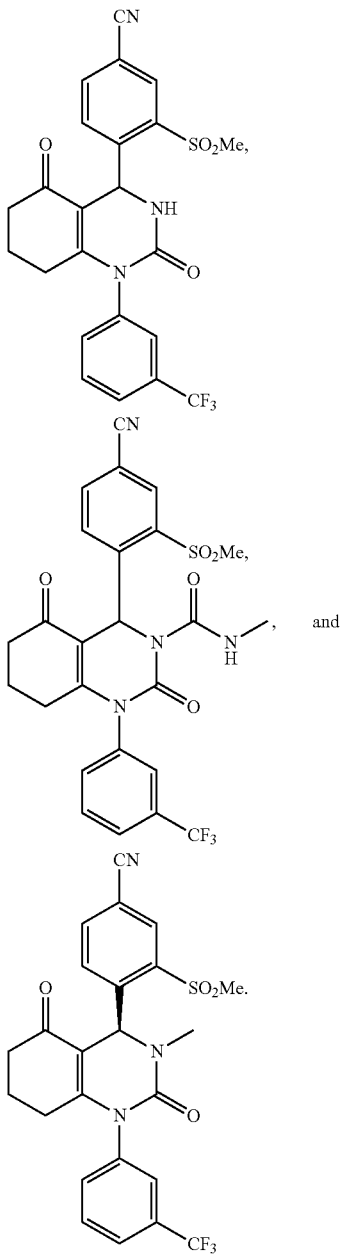

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, S(O), $S(O)_2$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk may be used in sub-formulas to indicate the bond which is connected to the core molecule as defined.

For example, the term "3-carboxypropyl-group" represents the following substituent:

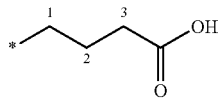

wherein the carboxy group is attached to the third carbon atom of the propyl group. The terms "1-methylpropyl-", "2,2-dimethylpropyl-" or "cyclopropylmethyl-" group represent the following groups:

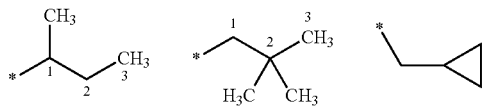

The asterisk may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

All isomeric forms (especially all stereoisomeric forms, e.g. all chiral, enantiomeric, diastereomeric and racemic forms, all tautomeric and all geometric isomeric forms) of a compound of the present invention are intended with this invention, unless the specific isomer is specifically indicated. Obviously, the isomer which is pharmacologically more potent and/or more efficacious is preferred.

It will be appreciated that the compounds of the present invention contain at least one asymmetrically substituted carbon atom, and may therefore be isolated as pure enantiomers or as a racemic or non-racemic mixture of both enantiomers. It will be appreciated that some of the compounds of the present invention contain more than one stereogenic center, that is more than one asymmetrically substituted carbon or sulfur atom, and may therefore be isolated as pure diastereomers or as diastereomeric mixtures, both in optically active or racemic forms.

The invention contemplates all conceivable stereoisomers, particularly the diastereomers and enantiomers mentioned herein, e.g. in substantially pure form, in enriched form (e.g. substantially free of any or all other undesired enantiomers and/or diastereomers and/or in any mixing ratio, including the racemic forms, as well as the salts thereof.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The term halogen generally denotes fluorine, chlorine, bromine and iodine.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (that is an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2''-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The above mentioned provision that a compound of formula 1 is not a compound selected from the above mentioned group means specifically that a compound of formula 1 is not a compound selected from a group consisting of

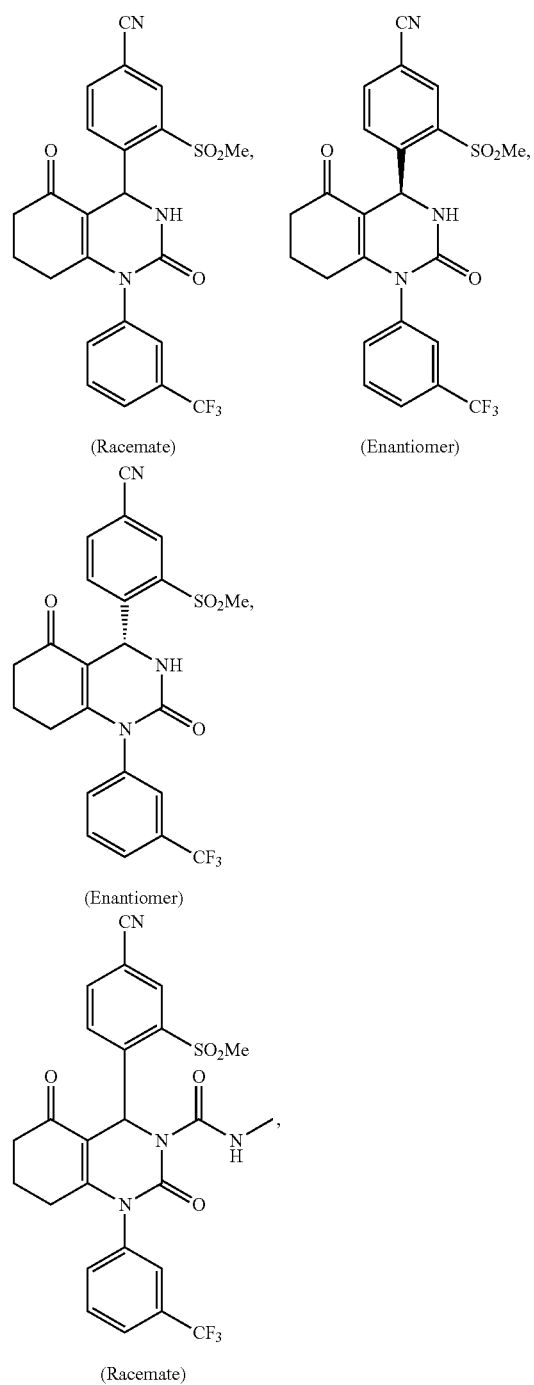

-continued

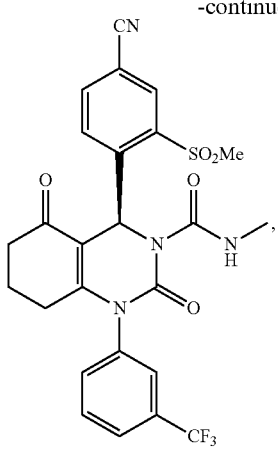
(Enantiomer)

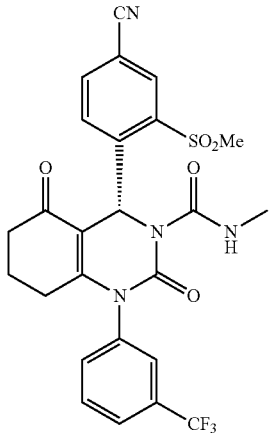
(Enantiomer) and

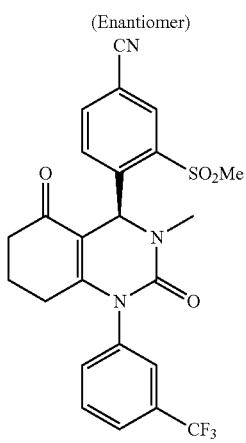
(Enantiomer)

which are disclosed in the European patent application No. 13157640.7.

Further Embodiments

Embodied are the above compounds of formula 1, wherein
$R^1$ is phenyl substituted with CN and
substituted with a second substituent $R^{11}$
$R^{1.1}$ is selected from the group consisting of
—SO$_2$—CH$_3$, —SO—CH$_3$ and —SO$_2$—CH$_2$CH$_2$—OH,
$R^2$ is phenyl substituted with CF$_3$
$R^3$ is selected from the group consisting of
H, CH$_3$ and —CH$_2$CH$_2$—OH.
or a pharmaceutically acceptable salt thereof,
provided that a compound of formula 1 is not a compound selected from the group consisting of

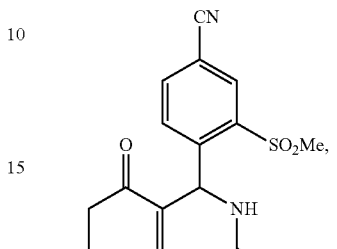

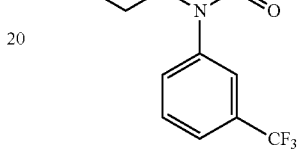

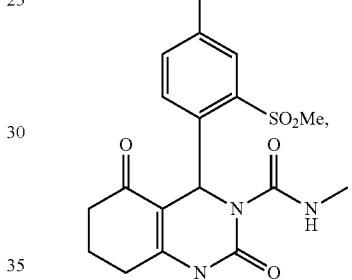
and

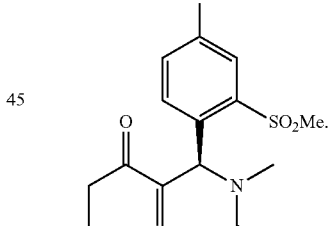

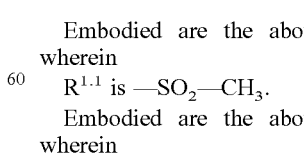

Embodied are the above compounds of formula 1, wherein
$R^{1.1}$ is —SO$_2$—CH$_3$.
Embodied are the above compounds of formula 1, wherein
$R^{1.1}$ is —SO—CH$_3$.
Embodied are the above compounds of formula 1, wherein
$R^{1.1}$ is —SO$_2$—CH$_2$CH$_2$—OH Embodied are the above compounds of formula 1, selected from the group consisting of compounds 1.a to 1.d.

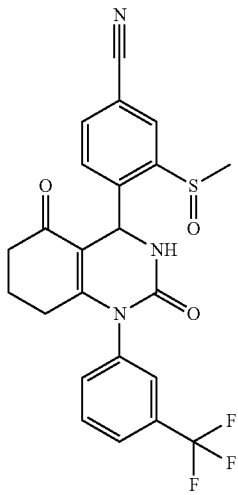

1.a

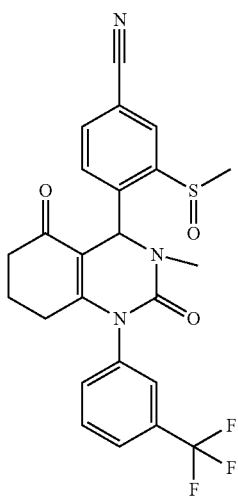

1.b

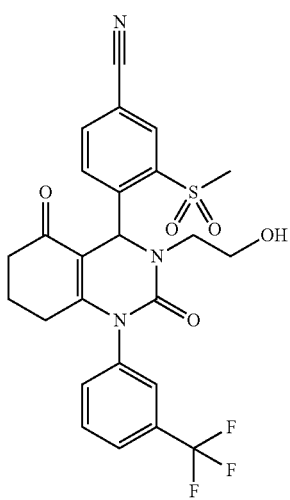

1.c

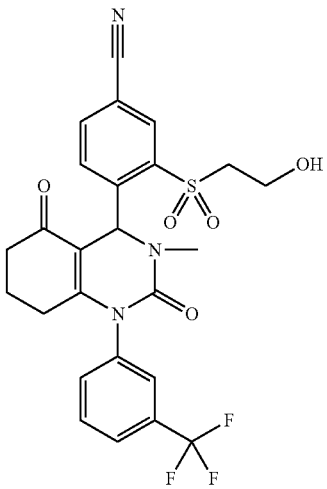

1.d

Embodied of all of the above mentioned embodiments of the invention is a compound of formula 1, wherein the configuration of formula 1 is formula 1'

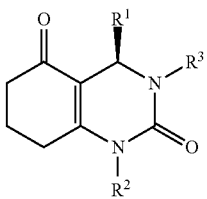

1' or a pharmaceutically acceptable salt thereof.

Another embodiment of the present invention is a compound of formula 1, for use as a medicament.

Another embodiment of the present invention is a compounds of formula 1, for use as a medicament for the treatment of asthma and allergic diseases, gastrointestinal inflammatory diseases, glomerulonephritis, eosinophilic diseases, chronic obstructive pulmonary disease, infection by pathogenic microbes and rheumatoid arthritis.

A further embodiment of the present invention is a compound of formula 1, for use as a medicament for the treatment of neutrophilic diseases, cystic fibrosis (CF), non-cystic fibrosis, idiopathic pulmonary fibrosis, bronchiectasis, ANCA-associated vasculitis, lung cancer, non-cyctic fibrosis bronchiectasis, emphysema, chronic bronchitis, acute lung injury (ALI), acute respiratory distress syndrome (ARDS), pulmonary hypertension, pulmonary arterial hypertension (PAH) and Alpha-1-antitrypsin deficiency (AATD.)

A further embodiment of the present invention is a compound of formula 1, for use as a medicament for the treatment of obesity and related inflammation, insulin resistance, diabetes, fatty liver and liver steatosis.

A further embodiment of the present invention is a compound of formula 1, for use as a medicament for the treatment of traumatic brain injury, abdominal aortic aneurism and Graft vs. Host Disease (GvHD).

A further embodiment of the present invention is a pharmaceutical composition containing one or more compounds of formula 1 or a pharmaceutically active salt thereof.

A further embodiment of the present invention is a method of treatment or prevention of diseases in which neutrophil elastase inhibitors have a therapeutic benefit, which method comprises administration of a therapeutically or preventively effective amount of a compounds of formula 1 to a patient in need thereof.

A further embodiment of the present invention is a pharmaceutical composition comprising additionally to a compound of formula 1, a pharmaceutically active compound selected from the group consisting of betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, but also combinations of two or three active substances.

Embodied are the above compounds of formula 1, wherein
$R^1$ is phenyl substituted with CN and
substituted with a second substituent $R^{1.1}$,
$R^{1.1}$ is selected from the group consisting of
—$SO_2$—$CH_3$, —SO—$CH_3$, —$CH_2$—OH, —$SO_2$—$CH_2CH_2$—OH, —$SO_2$—$CH_2CH_2$—$OCH_3$ and —$SO_2$—$CH_2CH_2CH_2$—OH Embodied are the above compounds of formula 1, wherein
$R^1$ is phenyl,
substituted with CN and
substituted with a second substituent $R^{1.1}$,
$R^{1.1}$ is selected from the group consisting of
—$SO_2$—$CH_3$, —SO—$CH_3$ and —$SO_2$—$CH_2CH_2$—OH, Embodied are the above compounds of formula 1, wherein
$R^1$ denotes a group of formula a.1

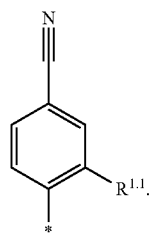

a.1

Embodied are the above compounds of formula 1, wherein
$R^2$ is phenyl substituted with $CF_3$.

Embodied are the above compounds of formula 1, wherein
$R^2$ is phenyl substituted with $CF_3$.

Embodied are the above compounds of formula 1, wherein
$R^2$ denotes a group of formula b.1

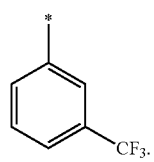

b.1

Embodied are the above compounds of formula 1, wherein
$R^3$ is selected from the group consisting of
H, $CH_3$, —CO—NH—$CH_3$, —$CH_2CH_2$—OH and —$CH_2$-oxetane.

Embodied are the above compounds of formula 1, wherein
$R^3$ is selected from the group consisting of
H, $CH_3$ and —$CH_2CH_2$—OH.

Embodied are the above compounds of formula 1, wherein
$R^3$ is H.

Embodied are the above compounds of formula 1, wherein
$R^3$ is $CH_3$.

Embodied are the above compounds of formula 1, wherein
$R^3$ is —$CH_2CH_2$—OH.

Embodied are the compounds of formula 1, wherein the compounds are selected from the group consisting of examples 2.1A, 2.2A, 4.3, 4.4, 5A and 6.

Embodied are the compounds of formula 1, wherein the compounds are selected from the group consisting of examples 2.1A, 2.2A, 4.3 and 6.

Any and each other of the definitions of $R^1$, $R^2$, $R^3$ and $R^{1.1}$ may be combined with each other.

Preparation

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used. The general processes for preparing the compounds according to the invention will become apparent to the one skilled in the art studying the following schemes. Starting materials are commercially available or may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

Compounds of the invention VI are accessible using the synthetic route illustrated in Scheme 1; $R^I$, $R^{E.1}$, $R^{E.2}$ have the meanings as defined hereinbefore and hereinafter.

SCHEME 1

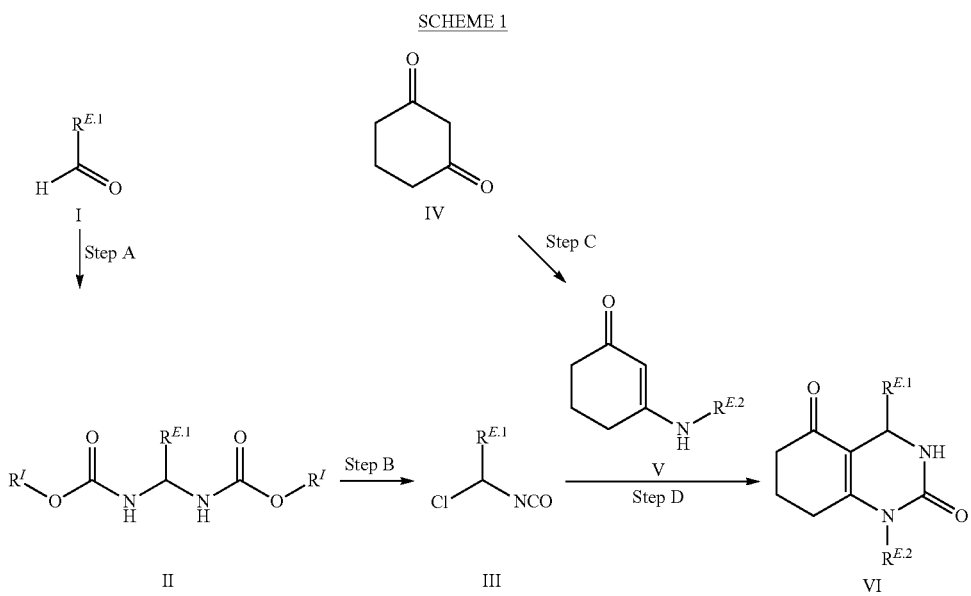

Intermediates II (Step A, intermediate I→intermediate II) can be prepared as described in Vovk et al. (*Synlett* 2006, 3, 375-378) or in PL2004/369318, by heating an aliphatic or aromatic aldehyde I with a carbamate, for example methyl carbamate, ethyl carbamate (urethane) or benzyl carbamate in the presence of a strong Brønsted or a Lewis acid, for example sulfuric acid, hydrogen chloride, p-toluenesulfonic acid, Amberlyst 15, tetrafluoroboric acid, trifluoroacetic acid or boron trifluoride, either without solvent as a melt or in a suitable solvent, such as benzene, toluene, acetonitrile, diethyl ether, chloroform, acetic anhydride or mixtures thereof. The reaction takes place within 1 to 24 hours. Preferred reaction temperatures are between room temperature and 160° C., or the boiling point of the solvent, respectively. Preferably the reaction is done with molten ethyl carbamate as reactant and a catalytic amount of concentrated sulfuric acid at temperatures of 140-160° C. without any further solvent.

The chlorination (Step B, intermediate II→intermediate III) can be done as described in Vovk et al. (*Synlett* 2006, 3, 375-378) and Sinitsa et al. (*J. Org. Chem. USSR* 1978, 14, 1107) by heating intermediate II together with a chlorinating agent, for example phosphorous pentachloride, phosphoryl chloride or sulfuryl chloride in an organic solvent, for example benzene or toluene. The reaction takes place within 1 to 24 hours. Preferred reaction temperatures are between 50° C. and 150° C.

Alternatively, intermediates III can be prepared as described in Jochims et al. (*Chem. Ber.* 1982, 115, 860-870) by α-halogenation of aliphatic isocyanates, for example benzyl isocyanate, using for example a bromination agent, for example N-bromosuccinimide. Isocyanates can be synthesized as described in U.S. Pat. No. 6,207,665 and in Charalambides et al. (*Synth. Commun.* 2007, 37, 1037-1044), by reacting an amine precursor with phosgene.

Intermediates V (Step C, intermediate IV→intermediates V) can be prepared as described in Ali et al. (*Aust. J. Chem.* 2005, 58, 870-876) and Scott et al. (*J. Med. Chem.* 1993, 36, 1947-1955) by direct condensation of cyclohexane-1,3-dione (IV) with an aliphatic or aromatic amine, optionally in a suitable solvent under reflux, for example benzene or toluene with azeotropic removal of water.

Alternatively, intermediates V can be prepared as described in Chen et al. (*Synth. Commun.* 2010, 40, 2506-2510) and Tietcheu et al. (*J. Heterocyclic Chem.* 2002, 39, 965-973) by reacting cyclohexane-1,3-dione (IV) and an aliphatic or aromatic amine in the presence of a catalyst, for example Ytterbium triflate [Yb(OTf)$_3$] or an acid, for example hydrogen chloride or p-toluenesulfonic acid, optionally in a solvent, for example water, acetic acid, acetonitrile, benzene, toluene. The reaction takes place within 1-24 hours. Preferred reaction temperatures are between room temperature and 120° C., most preferred room temperature.

Alternatively, intermediates V can be prepared in analogy to a procedure described in Mariano et al. (*J. Org. Chem.* 1984, 49, 220-228) by reacting an amine with 3-chloro-2-cyclohexen-1-one, which can be prepared from cyclohexane-1,3-dione.

Compounds according to the present invention (Step D, intermediates III→compounds of the invention VI) can be prepared as described in Vovk et al. (*Synlett* 2006, 3, 375-378), Vovk et al. (*Russ. J. Org. Chem.* 2010, 46, 709-715) and Kushnir et al. (*Russ. J. Org. Chem.* 2011, 47, 1727-1732) by reacting intermediates III with intermediates V in an organic solvent, for example dichloromethane, chloroform, benzene or toluene. The reaction takes place within 1-24 hours. Preferred reaction temperatures are between 0° C. and 100° C.

Compounds of the invention VI are alternatively accessible using the synthetic route illustrated in Scheme 2; $R^H$, $R^{E.1}$, $R^{E.2}$ have the meanings as defined hereinbefore and hereinafter.

SCHEME 2

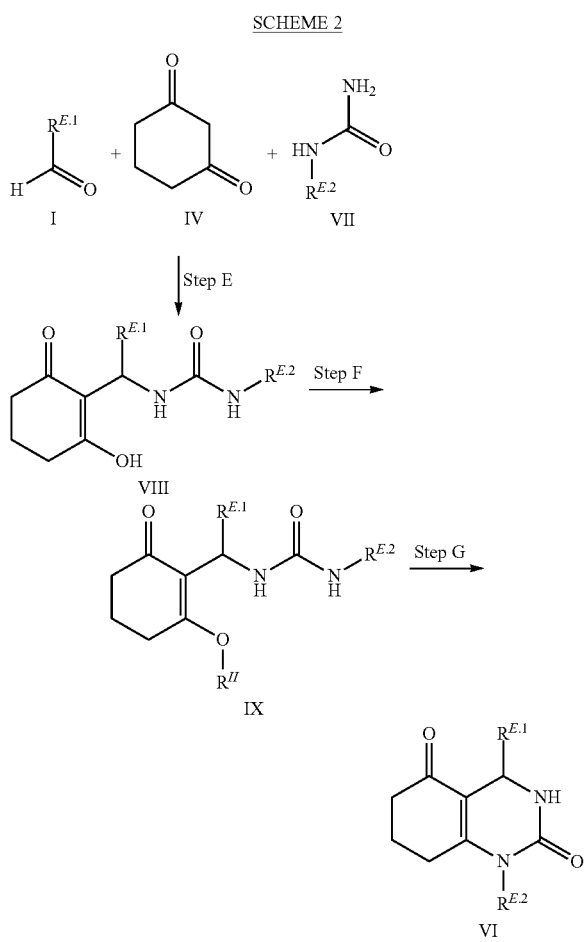

Intermediates VIII can be prepared following a procedure described in Zhu et al. (*Heterocycles* 2005, 65, 133-142) by reacting an aldehyde I with cyclohexane-1,3-dione (IV) and a substituted urea VII in the presence of trimethylsilyl chloride as Lewis acid in a mixture of acetonitrile and N,N-dimethylformamide. The reaction takes place within 1-72 hours. Preferred reaction temperatures are between room temperature and 100° C. Alternatively, as described amongst others in Kappe et al. (*Org. React.* 2004, 63, 1-116), other Brønsted or Lewis acids can be used as catalyst, for example HCl, $H_2SO_4$, citric acid, acetic acid, trifluoroacetic acid, para-toluenesulfonic acid, $H_3PO_4$, polyphosphoric acid, $Me_3SiI$, LiBr, $KHSO_4$, $Al_2O_3$, $HBF_4$, $BF_3.Et_2O$, $FeCl_2$, $SnCl_2$ or $SiO_2$ and the reaction can be carried out in other organic solvents, for example ethanol, methanol, tetrahydrofuran, acetic acid, 1-butyl-3-methylimidazolium bromide, acetic acetate, tert-butyl methyl ether, chloroform or in water. Alternatively, as described in US2011/34433, a suitable catalyst can be prepared by heating triethyl phosphate and phosphorouos pentoxide at 50° C. over night.

The alkylation of enol VIII (Step F, intermediates VII-I→intermediates IX) can be carried out by reacting the enol VIII with a suitable alkylating reagent, for example methyl iodide, ethyl bromide, dimethyl sulfate, diazomethane or trimethyloxonium tetrafluoroborate in the presence of a base, for example triethylamine, N,N-diisopropylethylamine, piperidine, pyridine, potassium carbonate, sodium hydroxide, potassium tert-butoxide, sodium hydride, lithium diisopropylamide, potassium hexamethyldisilazide, lithium hexamethyldisilazide, an organolithium reagent, for example tert-butyllithium or a Grignard reagent, for example isopropylmagnesiumchloride in an organic solvent, for example N,N-dimethylformamide, tetrahydrofuran, 1,4-dioxane, acetonitrile, dichloromethane, dimethylsulfoxide or toluene. The reaction takes place within 1-24 hours. Preferred reaction temperatures are between room temperature and 100° C.

Alternatively, the enol VIII can be activated by converting it into a sulfonylate, for example its corresponding methanesulfonylate, para-toluenesulfonylate or trifluoromethanesulfonylate by reacting it with the appropriate sulfonylating reagent, for example methanesulfonyl chloride or trifluoromethanesulfonic anhydride, optionally in the presence of a base, for example pyridine, triethylamine or N,N-diisopropylethylamine in an organic solvent, for example N,N-dimethylformamide, tetrahydrofuran, 1,4-dioxane, acetonitrile or dichloromethane.

Alternatively, the enol VIII can be activated as described in WO11094953 by converting it into its corresponding vinyl chloride using $POCl_3$ in chloroform.

The cyclization (Step G, intermediates IX→compounds of the invention VI) can be achieved by reacting an enolether IX with a suitable base, for example sodium or potassium tert-butoxide, sodium hydride, sodium hydroxide or lithium diisopropylamide in an organic solvent, for example dichloromethane, chloroform, N,N-dimethylformamide or acetonitrile. Alternatively, as described in Zanatta et al. (*Bioorg. Med. Chem. Lett.* 2006, 14, 3174-3184), para-toluenesulfonic acid can be used instead of abovementioned bases.

Compounds according to the present invention X are accessible via the synthetic routes depicted in scheme 3; $R^{E.1}$, $R^{E.2}$, $R^{E.3}$ have the meanings as defined hereinbefore and hereinafter.

SCHEME 3

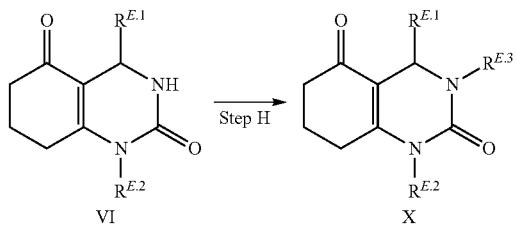

Compounds of the invention X (Step H, compounds of the invention VI→compounds of the invention X, $R^{E.3}$=alkyl) can be prepared as described in WO04024700 by reacting compounds of the invention VI with an alkylating agent, for example a dialkyl sulfate, for example dimethyl sulfate, an alkyl halide, for example methyl iodide or an alkyl sulfonylate, for example benzyl tosylate, in the presence of a suitable base, for example sodium hydride, sodium hydroxide, cesium carbonate, lithium diisopropylamide, potassium hexamethyldisilazide, lithium hexamethyldisilazide, an organolithium reagent, for example tert-butyllithium or a Grignard reagent, for example isopropylmagnesiumchloride, in an organic solvent, for example tetrahydrofuran, N,N-dimethylformamide, acetonitrile, 1,4-dioxane, dichloromethane or toluene. The reaction takes place within 1-72 hours. Preferred reaction temperatures are between 0° C. and 100° C.

Compounds according to the present invention XVI are accessible via the synthetic routes depicted in scheme 4; $R^{IV}$, $R^V$, $R^{E.1}$, $R^{E.2}$ have the meanings as defined hereinbefore and hereinafter.

SCHEME 4

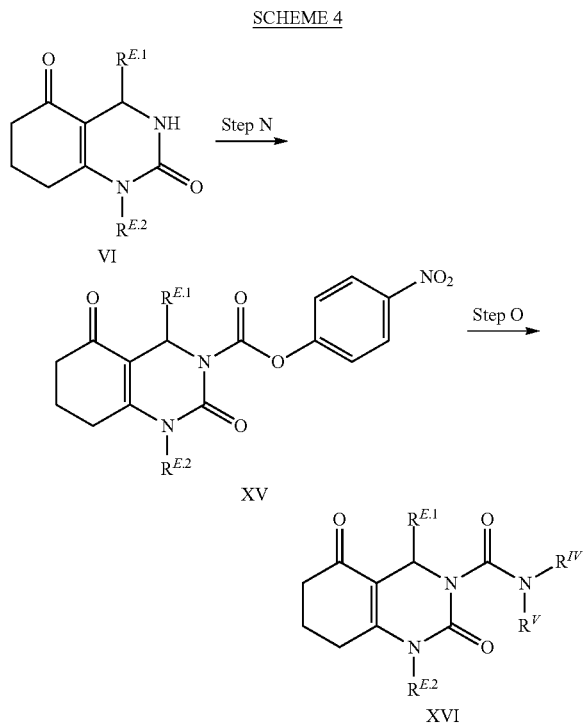

Intermediates XV (Step N, compounds of the invention VI→4-nitrophenyl carbamate intermediates XV) can be prepared as described in WO09080199, by reacting compounds of the invention VI with 4-nitrophenyl chloroformate in the presence of a base, for example triethylamine, N,N-diisopropylethylamine or N-methylmorpholine, optionally in the presence of a catalyst, for example 4-dimethylaminopyridine, in an organic solvent, for example dichloromethane, tetrahydrofuran, acetonitrile or N,N-dimethylformamide. The reaction takes place within 1-24 hours. Preferred reaction temperatures are between 0° C. and 50° C., most preferred room temperature.

Compounds of the invention XVI (Step 0, 4-nitrophenyl carbamate intermediates XV→compounds of the invention XVI) can be prepared as described in WO09080199, by reacting intermediates XV with an amine $R^{IV}NH_2$ or $R^{IV}R^VNH$ in an organic solvent, for example dichloromethane, acetonitrile, tetrahydrofuran, 1,4-dioxane, toluene or N,N-dimethylformamide. The reaction takes place within 1-72 hours. Preferred reaction temperatures are between 0° C. and 50° C., most preferred room temperature.

Additionally to the synthetic route depicted in Scheme 1, compounds of the invention VI are also accessible using the synthetic route depicted in Scheme 5, $R^{E.1}$, $R^{E.2}$ have the meanings as defined hereinbefore and hereinafter.

SCHEME 5

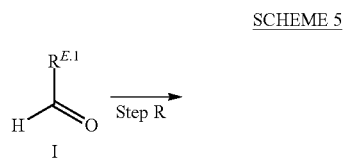

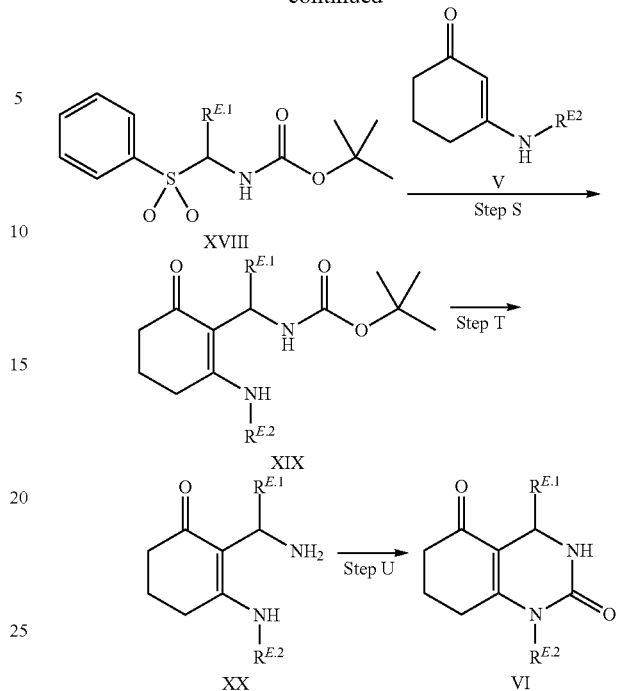

Intermediates XVIII (Step R, intermediate I→intermediate XVIII) can be prepared as described in Best et al. (*J. Am. Chem. Soc.* 2012, 134, 18193-18196) or in Yang et al. (*Org. Synth.* 2009, 86, 11-17), by reacting an aromatic aldehyde I with a suitable sulfinate, for example sodium benzenesulfinic acid, and a suitable carbamate, for example methyl carbamate or tert-butyl carbamate, in the presence of a suitable acid, for example formic acid, in a suitable solvent, for example tetrahydrofuran, ethanol, methanol or a mixture of solvents, for example tetrahydrofuran and water. Alternatively, as described in Reingruber et al. (*Adv. Synth. Catal.* 2009, 351, 1019-1024) or in WO06136305, a suitable lewis acid, for example trimethylsilyl chloride, can be used as acid and acetonitrile or toluene can be used as solvent. The reaction takes place within 1-6 days. Preferred reaction temperatures are between 0° C. and 50° C., most preferred room temperature.

Intermediates XIX (Step S, intermediate XVIII→intermediate XIX) can be prepared in analogy to the method described for the preparation of compounds of the invention VI (Scheme 1, Step D, intermediate III→compound of the invention VI), by reacting intermediates XVIII with intermediates V in the presence of a suitable base, for example sodium hydride or sodium tert-butoxide, in a suitable organic solvent, for example tetrahydrofuran or 2-methyltetrahydrofuran. The reaction takes place within 1-24 h. Preferred reaction temperatures are between 0° C. and 50° C., most preferred room temperature.

Intermediates XX (Step T, intermediate XIX→intermediate XX) can be prepared by reacting intermediates XIX with a suitable acid, for example hydrogen chloride, in a suitable solvent, for example 1,4-dioxane. The reaction takes place between 1-72 hours. Preferred reaction temperatures are between 0° C. and room temperature, most preferred room temperature.

Compounds of the invention VI (Step U, intermediate XX→compound of the invention VI) can be prepared as described in Csüitörtöki et al. (*Tetrahedron Lett.* 2011, 67, 8564-8571) or in WO11042145, by reacting intermediates XX with a suitable reagent, for example phosgene, triphosgene or carbonyl diimidazole, in the presence of a suitable base, for example triethylamine, N,N-diisopropylethylamine, pyridine or sodium carbonate, in a suitable solvent, for example acetonitrile, dichloromethane or toluene. The reaction takes place between 1-72 hours. Preferred reaction temperatures are between 0° C. and 50° C., most preferred room temperature.

Additionally to the synthetic route depicted in Scheme 2, compounds of the invention VI are also accessible using the synthetic route depicted in Scheme 6, $R^{E.1}$, $R^{E.2}$ have the meanings as defined hereinbefore and hereinafter.

SCHEME 6

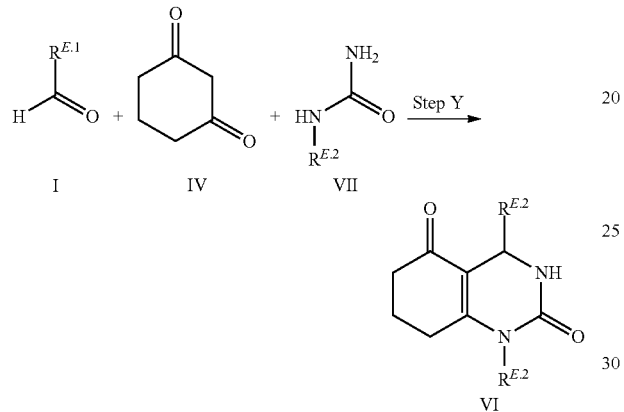

Compounds of the invention VI (Step Y, starting materials I, IV and VII→compounds of the invention VI) can be prepared following a procedure described in WO09080199 and WO05082864, by reacting an aldehyde I, a suitable 1,3-dione IV and an unsubstituted or monosubstituted urea VII with a reagent prepared by reacting a mixture of phosphorus pentoxide and a suitable trialkyl phosphate, for example triethyl phosphate at 50° C. over night, in a suitable solvent, for example tert-butyl methyl ether. The reaction takes place within 1-72 h. Preferred reaction temperatures are between room temperature and the boiling point of the employed solvent.

Compounds of the invention XXII are accessible via the synthetic routes depicted in scheme 7; $R^{E.2}$, $R^{E.3}$ have the meanings as defined hereinbefore and hereinafter.

SCHEME 7

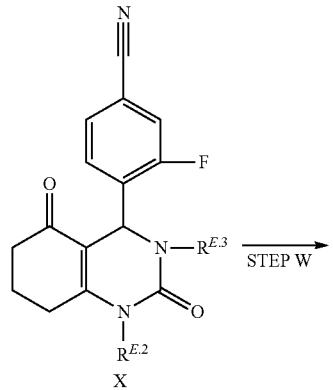

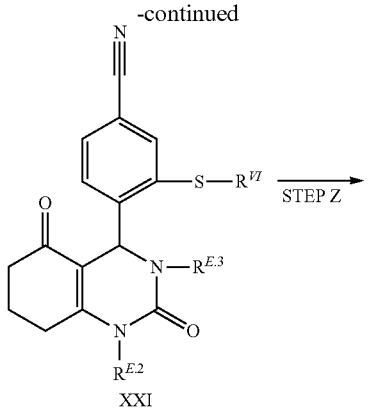

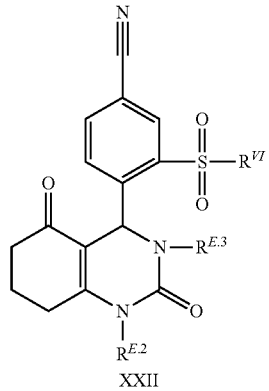

XXII

Intermediates XXI (Step W, fluoride intermediates X→sulfide intermediates XXI, $R^{E.3}$=H or alkyl) can be prepared by reacting intermediates X with a thiol compound $R^{VI}$SH in the presence of a suitable base, for example sodium hydride, sodium hydroxide, cesium carbonate, lithium diisopropylamide, potassium hexamethyldisilazide, lithium hexamethyldisilazide, an organolithium reagent, for example tert-butyllithium or a Grignard reagent, for example isopropylmagnesiumchloride, in an organic solvent, for example N,N-dimethylformamide, tetrahydrofuran, acetonitrile, 1,4-dioxane, dichloromethane or toluene. The reaction takes place within 1-72 hours. Preferred reaction temperatures are between 0° C. and 100° C.

Compounds of the invention XXII can be prepared by oxidation of sulfide intermediates XXI (Step Z, intermediates XXI→compounds of the invention XXII, $R^{E.3}$=H or alkyl) with an oxidating agent, for example hydrogen peroxide, 3-chloro-perbenzoic acid, periodic acid, sodium periodate, potassium permanganate, urea-hydrogen peroxide adduct, optionally in the presence of a metal catalyst, in a suitable solvent, for example dichloromethane, chloroform, methanol ethanol, water or mixtures thereof. The reaction takes place within 1-72 h. Preferred reaction temperatures are between room temperature and the boiling point of the employed solvent.

Sulfoxides can be prepared by oxidation of the corresponding sulfides with an oxidating agent, for example hydrogen peroxide, 3-chloro-perbenzoic acid, periodic acid, sodium periodate, tert-butyl hydroperoxide, urea-hydrogen peroxide adduct, optionally in the presence of a metal catalyst, for example methyltrioxorhenium, $FeCl_3$, $Sc(OTf)_3$, titanium (IV) complexes, in a suitable solvent, for example dichloromethane, chloroform, methanol ethanol, water or mixtures thereof. The reaction takes place within 1-72 h. Preferred reaction temperatures are between room temperature and the boiling point of the employed solvent.

Preliminary Remarks

The term room temperature denotes a temperature of about 20° C. As a rule, $^1$H NMR spectra and/or mass spectra have been obtained of the compounds prepared. Compounds given with a specific configuration at a stereocenter are isolated as pure isomers.

The retention times given are measured under the following conditions (TFA: trifluoroacetic acid, DEA: diethylamine, scCO$_2$: supercritical carbon dioxide):

Method Name: X012_S01
Column: Xbridge BEH C18, 2.1 × 30 mm, 1.7 μm
Column Supplier: Waters

| Gradient/Solvent Time [min] | % Solvent [H$_2$O, 0.1% TFA] | % Solvent [acetonitrile] | Flow [ml/min] | Temperature [° C.] |
|---|---|---|---|---|
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

Method Name: Z011_S03
Column: XBridge C18, 3 × 30 mm, 2.5 μm
Column Supplier: Waters

| Gradient/Solvent Time [min] | % Solvent [H$_2$O, 0.1% NH$_3$] | % Solvent [acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: Z018_S04
Column: Sunfire C18, 3 × 30 mm, 2.5 μm
Column Supplier: Waters

| Gradient/Solvent Time [min] | % Solvent [H$_2$O, 0.1% TFA] | % Solvent [acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: I_IA_15_MeOH_NH3
Column: Chiralpak IA 4.6 × 250 mm, 5 μm
Column Supplier: Daicel

| Gradient/Solvent Time [min] | % Solvent [MeOH, 20 mM NH$_3$] | % Solvent [scCO$_2$] | Flow [ml/min] | Temperature [° C.] | Back Pressure [bar] |
|---|---|---|---|---|---|
| 10 min | 15 | 85 | 4 | 40 | 120 |

Method Name: I_IA_20_MeOH_NH3
Column: Chiralpak IA 4.6 × 250 mm, 5 μm
Column Supplier: Daicel

| Gradient/Solvent Time [min] | % Solvent [MeOH, 20 mM NH$_3$] | % Solvent [scCO$_2$] | Flow [ml/min] | Temperature [° C.] | Back Pressure [bar] |
|---|---|---|---|---|---|
| 10 min | 20 | 80 | 4 | 40 | 120 |

Method Name: I_IA_25_MeOH_NH3
Column: Chiralpak IA 4.6 × 250 mm, 5 μm
Column Supplier: Daicel

| Gradient/Solvent Time [min] | % Solvent [MeOH, 20 mM NH$_3$] | % Solvent [scCO$_2$] | Flow [ml/min] | Temperature [° C.] | Back Pressure [bar] |
|---|---|---|---|---|---|
| 10 min | 25 | 75 | 4 | 40 | 120 |

Method Name: I_IC_30_MeOH_NH3
Column: Chiralpak IC 4.6 × 250 mm, 5 μm
Column Supplier: Daicel

| Gradient/Solvent Time [min] | % Solvent [MeOH, 20 mM NH$_3$] | % Solvent [scCO$_2$] | Flow [ml/min] | Temperature [° C.] | Back Pressure [bar] |
|---|---|---|---|---|---|
| 10 min | 30 | 70 | 4 | 40 | 150 |

Method Name: 005_CA01
Column: SunFire C18, 3.0 × 30 mm, 2.5 μm
Column Supplier: Waters

| Gradient/Solvent Time [min] | % Solvent [H$_2$O, 0.1% TFA] | % Solvent [acetonitrile] | Flow [ml/min] | Temperature [° C.] |
|---|---|---|---|---|
| 0.0 | 98 | 2 | 2.0 | 60.0 |
| 1.2 | 0 | 100 | 2.0 | 60.0 |
| 1.4 | 0 | 100 | 2.0 | 60.0 |

Method Name: X012_S02
Column: Xbridge BEH C18, 2.1 × 30 mm, 1.7 μm
Column Supplier: Waters

| Gradient/Solvent Time [min] | % Solvent [H$_2$O, 0.1% TFA] | % Solvent [acetonitrile] | Flow [ml/min] | Temperature [° C.] |
|---|---|---|---|---|
| 0.0 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

SYNTHESES OF INTERMEDIATES

Intermediate 1

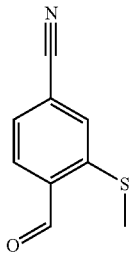

4-Formyl-3-methylsulfanyl-benzonitrile

Potassium carbonate (3.8 g; 27.2 mmol) is added to a solution of 4-cyano-2-fluorobenzaldehyde (2.0 g; 13.4 mmol) and sodium thiomethanolate (1.175 g; 16.8 mmol) in DMF (10 mL) and the mixture is stirred at 120° C. for 2 h. The reaction mixture is cooled with an ice bath. Water is added and the precipitate is filtered off, washed with water and dried. Yield: 1.98 g. ESI mass spectrum: [M+H]$^+$=178; Retention time HPLC: 0.731 min (Z011_S03).

Intermediate 2

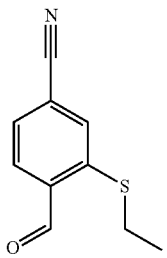

3-Ethylsulfanyl-4-formyl-benzonitrile

Intermediate 2 is prepared in analogous fashion as described for 4-formyl-3-methylsulfanyl-benzonitrile (INTERMEDIATE 1), replacing sodium thiomethanolate with sodium thioethanolate (reaction temperature 50° C.). ESI mass spectrum: [M+H]$^+$=192; Retention time HPLC: 0.81 min (Z011_S03).

Intermediate 3

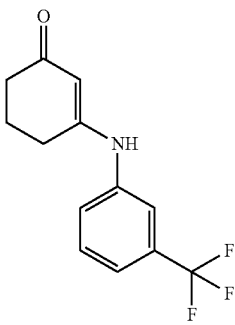 [SMILES: O=C1C=C(Nc2cccc(C(F)(F)F)c2)CCC1]

3-(3-Trifluoromethyl-phenylamino)-cyclohex-2-enone

Ytterbiumtriflate (138 mg; 0.223 mmol) is added to a solution of m-trifluoromethylaniline (5.55 mL; 44.6 mmol) and 1,3-cyclohexanedione (5.0 g; 44.6 mmol) and the mixture is stirred at room temperature for 1 h. Methanol is added to the suspension until everything is dissolved. Water is added and the precipitate is filtered off, washed with water and dried. Yield: 10.35 g. ESI mass spectrum: [M+H]$^+$=256; Retention time HPLC: 0.47 min (X012_S01).

Intermediate 4

{(4-Cyano-2-methylsulfanyl-phenyl)-[6-oxo-2-(3-trifluoromethyl-phenylamino)cyclohex-1-enyl]-methyl}-carbamic acid tert-butyl ester

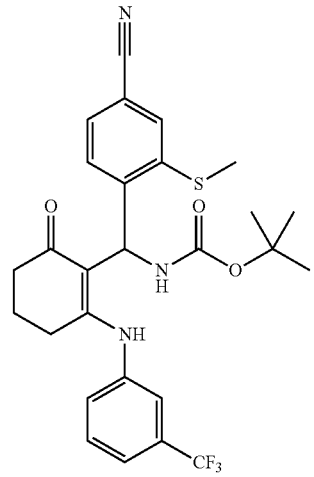 [SMILES: CSc1cc(C#N)ccc1C(NC(=O)OC(C)(C)C)C1=C(Nc2cccc(C(F)(F)F)c2)CCCC1=O]

Step 1

[Benzenesulfonyl-(4-cyano-2-methylsulfanyl-phenyl)-methyl]-carbamic acid tert-butyl ester Formic acid (3.0 mL, 79 mmol) is added to a solution of tert-butyl carbamate (1.436 g, 12.3 mmol), 4-formyl-3-methylsulfanyl-benzonitrile (INTERMEDIATE 1; 1.975 g, 11.1 mmol) and sodium benzenesulfinate (2.012 g, 12.2 mmol) in a mixture of THF (3.0 mL) and water (7 mL), and the mixture is stirred at room temperature for 3 days. Water is added, the precipitate is filtered off and washed with water. The precipitate is treated with tert-butyl methyl ether, and the mixture is stirred for 30 min. The precipitate is filtered off, washed with tert-butyl methyl ether and dried. Yield: 3.5 g.

Step 2

{(4-Cyano-2-methylsulfanyl-phenyl)-[6-oxo-2-(3-trifluoromethyl-phenylamino)cyclohex-1-enyl]-methyl}-carbamic acid tert-butyl ester Sodium hydride (60% in mineral oil, 154 mg, 3.85 mmol) is added in portions to a mixture of 3-(3-trifluoromethyl-phenylamino)-cyclohex-2-enone (INTERMEDIATE 3; 960 mg, 3.76 mmol) and 2-methyltetrahydrofuran (8 mL). After 30 min [benzenesulfonyl-(4-cyano-2-methylsulfanyl-phenyl)-methyl]-carbamic acid tert-butyl ester (Step 1, 1.56 g, 3.73 mmol) is added and the mixture is stirred at room temperature for 50 min. Water and 2-methyltetrahydrofuran are added and the phases are separated. The organic phase is dried over Na$_2$SO$_4$ and concentrated under reduced pressure. Yield: 2.13 g. ESI mass spectrum: [M+H]$^+$=532; Retention time HPLC: 1.22 min (Z018_S04).

Intermediate 5

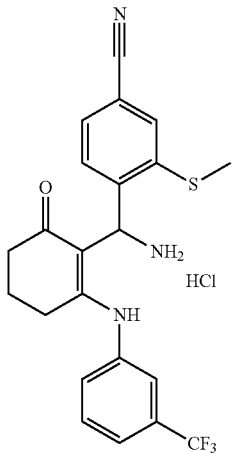 [SMILES: CSc1cc(C#N)ccc1C(N)C1=C(Nc2cccc(C(F)(F)F)c2)CCCC1=O ; Cl]

4-{Amino-[6-oxo-2-(3-trifluoromethyl-phenylamino)-cyclohex-1-enyl]-methyl}-3-methylsulfanyl-benzonitrile hydrochloride A solution of hydrogen chloride in 1,4-dioxane (4 M, 4.5 mL, 18 mmol) is added to a mixture of {(4-cyano-2-methylsulfanyl-phenyl)-[6-oxo-2-(3-trifluoromethyl-phenylamino)cyclohex-1-enyl]-methyl}-carbamic acid tert-butyl ester (INTERMEDIATE 4, 2.16 g, 3.25 mmol) in acetonitrile (4.5 mL) and the mixture is stirred at room temperature for 1 h. The precipitate is filtered off, washed with acetonitrile and dried. Yield: 1.19 g. ESI mass spectrum: [M+H-NH$_3$]$^+$=415; Retention time HPLC: 0.88 min (Z018_S04).

Intermediate 6

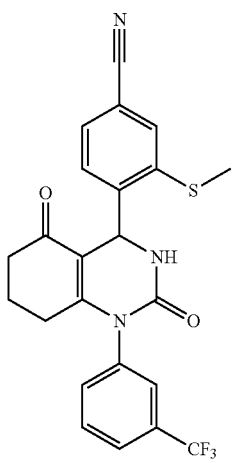 [SMILES: CSc1cc(C#N)ccc1C1NC(=O)N(c2cccc(C(F)(F)F)c2)C2=C1C(=O)CCC2]

4-[2,5-Dioxo-1-(3-trifluoromethyl-phenyl)-1,2,3,4,5,6,7,8-octahydro-quinazolin-4-yl]-3-methylsulfanyl-benzonitrile Triethylamine (89 µL, 0.634 mmol) is added to a mixture of 4-{amino-[6-oxo-2-(3-trifluoromethyl-phenylamino)-cyclohex-1-enyl]-methyl}-3-methylsulfanyl-benzonitrile hydrochloride (INTERMEDIATE 5, 1.19 g, 2.54 mmol) and 1,1'-carbonyldiimidazole (480 mg, 2.96 mmol) in acetonitrile (4 mL) and the mixture is stirred at room temperature for 15 min. The reaction mixture is evaporated. Water is added, the precipitate is filtered and washed with water. The residue is dissolved in dichloromethane and evaporated. Yield: 1.02 g. ESI mass spectrum: [M+H]$^+$=458; Retention time HPLC: 1.05 min (Z018_S04).

Intermediate 7

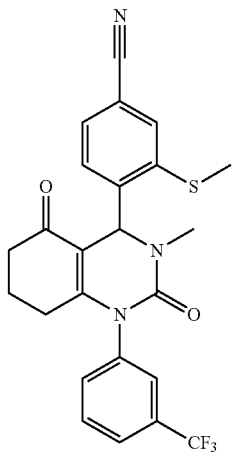 [SMILES: CSc1cc(C#N)ccc1C1C2=C(CCCC2=O)N(c2cccc(C(F)(F)F)c2)C(=O)N1C]

4-[3-Methyl-2,5-dioxo-1-(3-trifluoromethyl-phenyl)-1,2,3,4,5,6,7,8-octahydro-quinazolin-4-yl]-3-methylsulfanyl-benzonitrile Methyliodide (70 µL, 1.10 mmol) is added to a mixture of 4-[2,5-dioxo-1-(3-trifluoromethyl-phenyl)-1,2,3,4,5,6,7,8-octahydro-quinazolin-4-yl]-3-methylsulfanyl-benzonitrile (INTERMEDIATE 6; 177 mg; 0.354 mmol) and cesium carbonate (300 mg, 0.921 mmol) in DMF (2.4 mL) and the mixture is stirred at room temperature for 2 h. During the reaction, more cesium carbonate is added in small portions (total of 700 mg; 2.15 mmol). The reaction mixture is filtered and the filtrate is purified by reversed phase HPLC (Sunfire, gradient of acetonitrile in water, 0.1% TFA). Yield: 26 mg. ESI mass spectrum: [M+H]$^+$=472; Retention time HPLC: 1.10 min (Z018_S04).

Intermediate 8

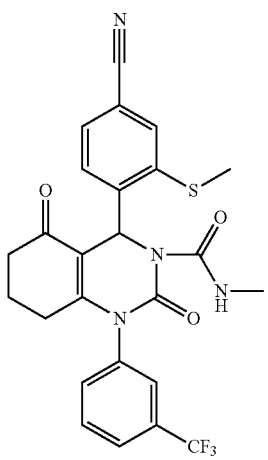 [SMILES: CNC(=O)N1C(=O)N(c2cccc(C(F)(F)F)c2)C2=C(C(=O)CCC2)C1c1ccc(C#N)cc1SC]

4-(4-Cyano-2-methylsulfanyl-phenyl)-2,5-dioxo-1-(3-trifluoromethyl-phenyl)-1,4,5,6,7,8-hexahydro-2H-quinazoline-3-carboxylic acid methylamide To a mixture of 4-[2,5-dioxo-1-(3-trifluoromethyl-phenyl)-1,2,3,4,5,6,7,8-octahydroquinazoline-4-yl]-3-methylsulfanyl-benzonitrile (INTERMEDIATE 6; 82 mg; 0.179 mmol) and diisopropylethylamine (100 μL; 0.588 mmol) in acetonitrile (1 mL) is added 4-nitrophenylchloroformate (170 mg; 0.843 mmol) and 4-dimethylaminopyridine (210 mg; 1.719 mmol) in little portions over 19 h at room temperature. Methylamine (1M in THF; 1 mL; 1.00 mmol) is added to the mixture containing the 4-nitro-phenyl carbamate intermediate and the mixture is stirred at room temperature for 30 min. The reaction mixture is purified by reversed phase HPLC (Sunfire, gradient of acetonitrile in water, 0.1% TFA). Yield: 63 mg. ESI mass spectrum: [M+H]$^+$=515; Retention time HPLC: 1.11 min (Z018_S04).

Intermediate 9

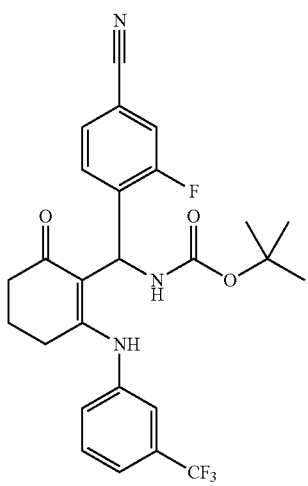 [SMILES: CC(C)(C)OC(=O)NC(C1=C(Nc2cccc(C(F)(F)F)c2)CCCC1=O)c1ccc(C#N)cc1F]

{(4-Cyano-2-fluoro-phenyl)-[6-oxo-2-(3-trifluoromethyl-phenylamino)-cyclopent-1-enyl]-methyl}-carbamic acid tert-butyl ester INTERMEDIATE 9 is prepared in analogous fashion as described for INTERMEDIATE 4, replacing 4-formyl-3-methylsulfanyl-benzonitrile with 3-fluoro-4-formyl-benzonitrile as starting material in Step 1. ESI mass spectrum: [M+H]$^+$=504; Retention time HPLC: 1.19 min (Z018_S04).

Intermediate 10

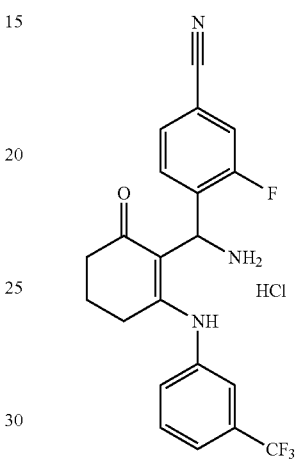

4-{Amino-[6-oxo-2-(3-trifluoromethyl-phenylamino)-cyclohex-1-enyl]-methyl}-3-fluoro-benzonitrile hydrochloride INTERMEDIATE 10 is prepared in analogous fashion as described for INTERMEDIATE 5, replacing INTERMEDIATE 4 with INTERMEDIATE 9 as starting material. ESI mass spectrum: [M+H-NH$_3$]$^+$=387; Retention time HPLC: 0.84 min (Z018_S04).

Intermediate 11

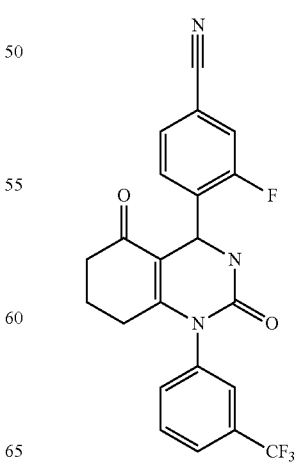

4-[2,5-Dioxo-1-(3-trifluoromethyl-phenyl)-1,2,3,4,5,6,7,8-octahydro-quinazolin-4-yl]-3-fluoro-benzonitrile INTERMEDIATE 11 is prepared in analogous fashion as described for INTERMEDIATE 6, replacing INTERMEDIATE 5 with INTERMEDIATE 10 as starting material. ESI mass spectrum: [M+H]$^+$=430; Retention time HPLC: 1.01 min (Z018_S04).

Intermediate 12

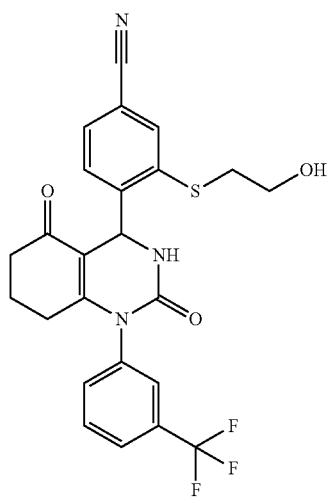 [SMILES: N#Cc1ccc(C2NC(=O)N(c3cccc(C(F)(F)F)c3)C3=C2C(=O)CCC3)c(SCCO)c1]

4-[2,5-Dioxo-1-(3-trifluoromethyl-phenyl)-1,2,3,4,5,6,7,8-octahydro-quinazolin-4-yl]-3-(3-hydroxy-ethylsulfanyl)-benzonitrile 2-Mercapto-1-ethanol (27 μL, 0.38 mmol) is added to a mixture of sodium hydride (55% in mineral oil, 16.0 mg, 0.37 mmol) in DMF (0.20 mL) at 0° C. After stirring for 20 min at 0° C., a solution of 4-[2,5-dioxo-1-(3-trifluoromethyl-phenyl)-1,2,3,4,5,6,7,8-octahydro-1H-cyclohexapyrimidin-4-yl]-3-fluoro-benzonitrile (INTERMEDIATE 11, 155 mg, 0.32 mmol) in DMF (0.70 mL) is added and the mixture is stirred at room temperature for 2 h. Water is added and after acidification with acetic acid the mixture is purified by reversed phase HPLC (Waters SunFire™-C$_{18}$, gradient of acetonitrile in water, 0.1% TFA). Yield: 18 mg. ESI mass spectrum: [M+H]$^+$=488; Retention time HPLC: 0.98 min (Z018_S04).

Intermediates 12.1-12.2 are prepared in analogous fashion as described for INTERMEDIATE 12, using the appropriate thiols as starting material, respectively.

| INTER-MEDI-ATE | R$^{1.1}$ | MS [M + H]$^+$ | Retention time [min] | HPLC-Method |
|---|---|---|---|---|
| 12.1 | ---S~~~OH | 502 | 0.99 | Z018_S04 |
| 12.2 | ---S~~~O~ | 502 | 1.06 | Z018_S04 |

Intermediate 13

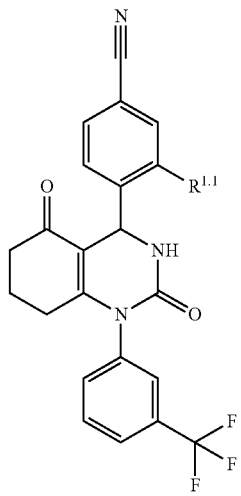

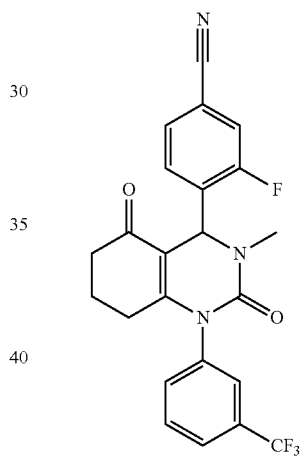

3-Fluoro-4-[3-methyl-2,5-dioxo-1-(3-trifluoromethyl-phenyl)-1,2,3,4,5,6,7,8-octahydro-quinazolin-4-yl]-benzonitrile To a mixture of 4-[2,5-dioxo-1-(3-trifluoromethyl-phenyl)-1,2,3,4,5,6,7,8-octahydro-1H-cyclohexapyrimidin-4-yl]-3-fluoro-benzonitrile (INTERMEDIATE 11, 626 mg, 1.46 mmol) and cesium carbonate (1.27 g, 3.90 mmol) in DMF (4.0 mL) is added methyl iodide (370 μL, 5.81 mmol) and the mixture is stirred at room temperature for 150 min. Water is added to the reaction mixture, the precipitate is filtered off, washed with water and dried. Yield: 472 mg; ESI mass spectrum [M+H]$^+$=444; Retention time HPLC: 1.07 min (Z018_S04).

Intermediates 14.1-14.3 are prepared in analogous fashion as described for INTERMEDIATE 12, replacing INTERMEDIATE 11 with INTERMEDIATE 13 and using the appropriate thiols as starting material, respectively.

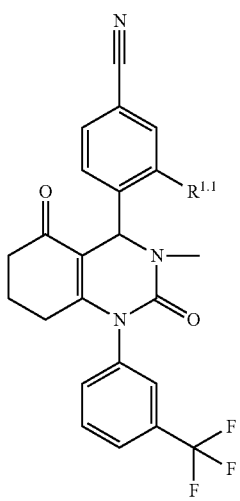

| INTER-MEDI-ATE | R[1.1] | MS [M + H]+ | Retention time [min] | HPLC-Method |
|---|---|---|---|---|
| 14.1 | ---S~~~OH | 502 | 1.02 | Z018_S04 |
| 14.2 | ---S~~~~OH | 516 | 1.02 | Z018_S04 |
| 14.3 | ---S~~~O~ | 516 | 1.10 | Z018_S04 |

Intermediate 15

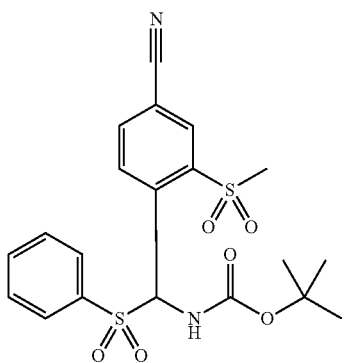 [SMILES: CC(C)(C)OC(=O)NC(c1ccc(C#N)cc1S(C)(=O)=O)S(=O)(=O)c1ccccc1]

tert-Butyl (4-Cyano-2-(methylsulfonyl)phenyl)(phenylsulfonyl)methylcarbamate

Formic acid (6.2 mL, 164 mmol) is added to a mixture of tert-butyl carbamate (3.05 g, 26.0 mmol), 4-formyl-3-(methylsulfonyl)benzonitrile (5.44 g, 26.0 mmol, preparation according to WO09080199) and sodium benzenesulfinate (4.27 g, 26.0 mmol) in THF (10.0 mL) and water (25.0 mL) and the reaction mixture is stirred at room temperature for 4 days. Water (30 mL) is added and the precipitate is filtered off, washed with water and acetonitrile and dried. Yield: 5.10 g. ESI mass spectrum: [M+H]+=451; Retention time HPLC: 0.59 min (X012_S01).

Intermediate 16

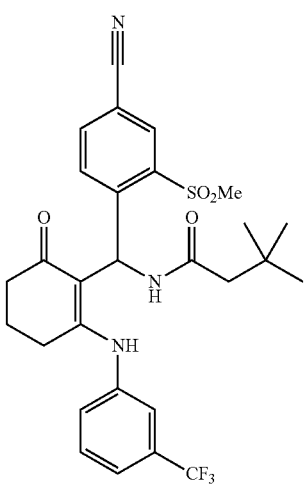 [SMILES: CC(C)(C)CC(=O)NC(C1=C(Nc2cccc(C(F)(F)F)c2)CCCC1=O)c1ccc(C#N)cc1S(C)(=O)=O]

{(4-Cyano-2-methanesulfonyl-phenyl)-[6-oxo-2-(3-trifluoromethyl-phenylamino)cyclohex-1-enyl]-methyl}-carbamic acid tert-butyl ester Sodium hydride (60% in mineral oil, 82.5 mg, 2.06 mmol) is added in portions to a mixture of 3-(3-trifluoromethyl-phenylamino)-cyclohex-2-enone (INTERMEDIATE 3, 526 mg, 2.06 mmol) and 2-methyltetrahydrofuran (9.0 mL). After 20 min tert-butyl (4-cyano-2-(methylsulfonyl)phenyl)(phenylsulfonyl)methylcarbamate (INTERMEDIATE 15, 860 mg, 1.72 mmol) is added and the reaction mixture is stirred at room temperature for 1 h and concentrated under reduced pressure. The residue is treated with water and extracted with ethyl acetate. The organic phase is concentrated under reduced pressure and the crude product is purified by flash chromatography on silica (gradient petrolether/ethyl acetate 80/20 to 50/50). Yield: 976 mg; ESI mass spectrum [M+H]+=564; Retention time HPLC: 0.72 min (X012_S01).

Intermediate 17

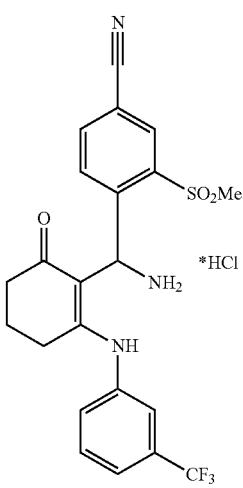 [SMILES: CS(=O)(=O)c1cc(C#N)ccc1C(N)C1=C(Nc2cccc(C(F)(F)F)c2)CCCC1=O]

4-{Amino-[6-oxo-2-(3-trifluoromethyl-phenylamino)-cyclohex-1-enyl]-methyl}-3-methanesulfonyl-benzonitrile hydrochloride To a solution of {(4-cyano-2-methanesulfonyl-phenyl)-[6-oxo-2-(3-trifluoromethyl-phenylamino)-cyclohex-1-enyl]-methyl}-carbamic acid tert-butyl ester (INTERMEDIATE 16, 976 mg, 1.73 mmol) in 1,4-dioxane (2.0 mL) is added a solution of hydrogen chloride in 1,4-dioxane (4 M, 3.46 mL, 13.85 mmol) and the mixture is stirred at room temperature for 3 h. The reaction mixture is diluted with tert-butylmethylether and the precipitate is filtered off, washed with tert-butylmethylether and dried. Yield: 529 mg. ESI mass spectrum: [M+H]$^+$=464; Retention time HPLC: 0.47 min (X012_S01).

Intermediate 18

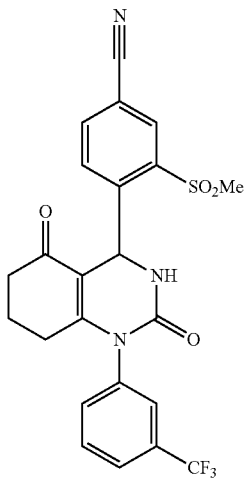 [SMILES: CS(=O)(=O)c1cc(C#N)ccc1C1NC(=O)N(c2cccc(C(F)(F)F)c2)C2=C1C(=O)CCC2]

4-[2,5-Dioxo-1-(3-trifluoromethyl-phenyl)-1,2,3,4,5,6,7,8-octahydro-quinazolin-4-yl]-3-methanesulfonyl-benzonitrile To a solution of 4-{amino-[6-oxo-2-(3-trifluoromethyl-phenylamino)-cyclohex-1-enyl]-methyl}-3-methanesulfonyl-benzonitrile hydrochloride (INTERMEDIATE 17, 529 mg, 0.95 mmol) in acetonitrile (5.0 mL) is added 1,1'-carbonyldiimidazole (192 mg, 1.19 mmol) and triethylamine (33 µL, 0.24 mmol). After stirring at room temperature overnight, the reaction mixture is concentrated under reduced pressure. The residue is treated with water and the precipitate is filtered off, washed with water and dried. Yield: 468 mg. ESI mass spectrum: [M+H]$^+$=490; Retention time HPLC: 0.57 min (X012_S01).

Intermediate 19

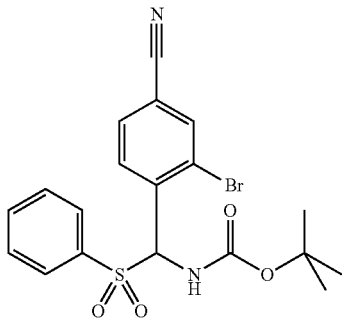 [SMILES: CC(C)(C)OC(=O)NC(c1ccc(C#N)cc1Br)S(=O)(=O)c1ccccc1]

[Benzenesulfonyl-(2-bromo-4-cyano-phenyl)-methyl]-carbamic acid tert-butyl ester 3-Bromo-4-formyl-benzonitrile (20.5 g, 97.7 mmol), benzenesulfinic acid sodium salt (16.03 g, 97.6 mmol) and tert-butylcarbamate (11.4 g, 97.7 mmol) are suspended in water (312 mL) and THF (78 mL). Formic acid (28.8 g, 625 mmol) is added and the solution is stirred at room temperature for 6 days. Water (300 mL) is added and the precipitate is filtered off, washed with water and dried. The crude product is further purified by precipitation from tert-butylmethylether. Yield: 26.8 g; ESI mass spectrum: [M+Na]$^+$=473 (bromine isotope pattern).

Intermediate 20

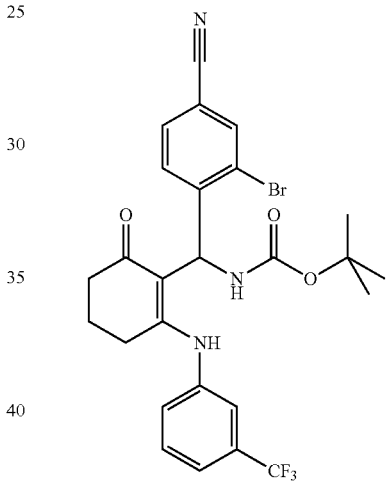

{(2-Bromo-4-cyano-phenyl)-[6-oxo-2-(3-trifluoromethyl-phenylamino)-cyclohex-1-enyl]-methyl}-carbamic acid tert-butyl ester 3-(3-Trifluoromethyl-phenylamino)-cyclohex-2-enone (INTERMEDIATE 3, 10.7 g, 42 mmol) is suspended in 2-methyl-tetrahydrofurane (150 mL) and sodium hydride (60% in mineral oil) (1.76 g, 43.9 mmol) is added in portions. The mixture is stirred at room temperature for 20 min and [benzenesulfonyl-(2-bromo-4-cyano-phenyl)-methyl]-carbamic acid tert-butyl ester (INTERMEDIATE 19, 16.5 g, 36.6 mmol) is added. The mixture is stirred for 1 h at room temperature. The organic phase is washed with water, dried over MgSO$_4$ and concentrated. The product is precipitated from cyclohexane. Yield: 20.6 g. ESI mass spectrum: [M+H]$^+$=564 (bromine isotope pattern); Retention time HPLC: 0.81 min (X012_S02).

Intermediate 21

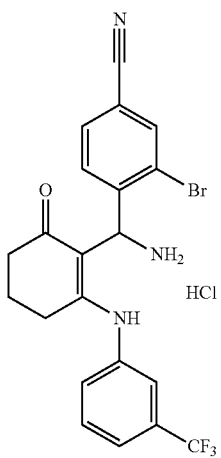 [SMILES: N#Cc1ccc(C(N)C2=C(Nc3cccc(C(F)(F)F)c3)CCCC2=O)c(Br)c1 ; Cl]

4-{Amino-[6-oxo-2-(3-trifluoromethyl-phenylamino)-cyclohex-1-enyl]-methyl}-3-bromo-benzonitrile hydrochloride {(2-Bromo-4-cyano-phenyl)-[6-oxo-2-(3-trifluoromethyl-phenylamino)-cyclohex-1-enyl]-methyl}-carbamic acid tert-butyl ester (INTERMEDIATE 20, 20.8 g, 36.9 mmol) is suspended in acetonitrile (150 mL) and a solution of hydrogen chloride in 1,4-dioxane (4 M, 46.1 mL, 184.3 mmol) is added. The mixture is stirred at room temperature for 3 h. The product precipitates from the reaction mixture. The precipitate is filtered off, washed with acetonitrile and dried. Yield: 16.5 g ESI mass spectrum: [M+H]$^+$=464 (bromine isotope pattern), Retention time HPLC: 0.56 min, (X012_S02).

Intermediate 22

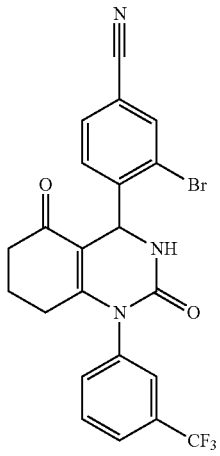 [SMILES: CN1C(=O)N(c2cccc(C(F)(F)F)c2)C2=C(C(=O)CCC2)C1c1ccc(C#N)cc1Br]

3-Bromo-4-[2,5-dioxo-1-(3-trifluoromethyl-phenyl)-1,2,3,4,5,6,7,8-octahydro-quinazolin-4-yl]-benzonitrile 4-{Amino-[6-oxo-2-(3-trifluoromethyl-phenylamino)-cyclohex-1-enyl]-methyl}-3-bromo-benzonitrile (INTERMEDIATE 21, 16.5 g, 33 mmol) is suspended in acetonitrile (150 mL) and triethylamine (3.47 mL, 24.7 mmol) and 1,1'-carbonyldiimidazole (6.7 g, 41.2 mmol) are added. The mixture is stirred at room temperature for 1 h. The solvent is evaporated under reduced pressure and water is added. The product precipitates; the precipitate is filtered off, washed with water and dried. Yield: 14 g. ESI mass spectrum: [M+H]$^+$=490 (bromine isotope pattern); Retention time HPLC: 0.64 min (X012_S02).

Intermediate 23

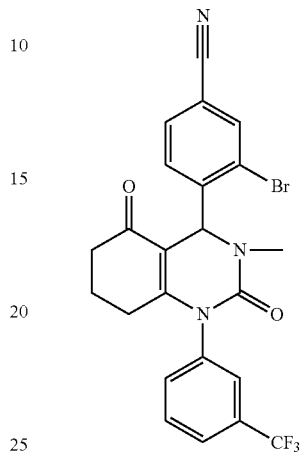

3-Bromo-4-[3-methyl-2,5-dioxo-1-(3-trifluoromethyl-phenyl)-1,2,3,4,5,6,7,8-octahydro-quinazolin-4-yl]-benzonitrile Methyliodide (3.55 mL, 57.1 mmol) is added to a mixture of 3-bromo-4-[2,5-dioxo-1-(3-trifluoromethyl-phenyl)-1,2,3,4,5,6,7,8-octahydro-quinazolin-4-yl]-benzonitrile (INTERMEDIATE 22, 14.0 g, 28.6 mmol) and cesium carbonate (18.6 g, 57.1 mmol) in DMF (140 mL). The mixture is stirred at room temperature for 90 min. Ethyl acetate is added and the organic phase is washed with water three times, dried over MgSO$_4$ and concentrated. The crude product is purified by flash chromatography on silica (cyclohexane/ethyl acetate 30:70). Yield: 13.4 g. ESI mass spectrum: [M+H]$^+$=504 (bromine isotope pattern); Retention time HPLC: 0.70 min (X012_S02).

Intermediate 24

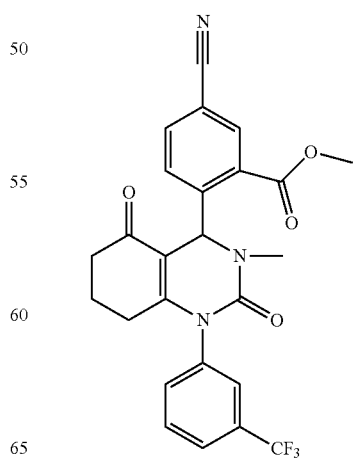

5-Cyano-2-[3-methyl-2,5-dioxo-1-(3-trifluoromethyl-phenyl)-1,2,3,4,5,6,7,8-octahydro-quinazolin-4-yl]-benzoic acid methyl ester 3-Bromo-4-[3-methyl-2,5-dioxo-1-(3-trifluoromethyl-phenyl)-1,2,3,4,5,6,7,8-octahydro-quinazolin-4-yl]-benzonitrile (INTERMEDIATE 23, 10.5 g, 20.8 mmol), 1.1-bis(diphenylphosphino)-ferrocen (1.15 g, 2.08 mmol), palladium acetate (233 mg, 1.04 mmol) and sodium acetate (5.12 g, 62.5 mmol) are suspended in methanol (180 mL) and treated with carbon monoxide at 5 bar and 100° C. for 40 h. The product begins to crystallize from the reaction mixture. Diisopropylether and dichloromethane are added and further crystals are collected. Further purification is performed by recrystallization from methanol and by flash chromatography on silica (dichloromethane/methanol 99:1). Yield: 1.7 g. ESI mass spectrum: [M+H]$^+$=484; Retention time HPLC: 0.68 min (X012_S02).

Intermediate 25

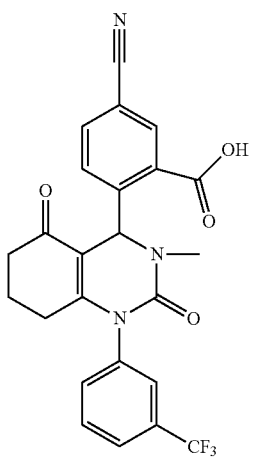 [SMILES: CN1C(=O)N(c2cccc(C(F)(F)F)c2)C2=C(C(=O)CCC2)C1c1ccc(C#N)cc1C(=O)O]

5-Cyano-2-[3-methyl-2,5-dioxo-1-(3-trifluoromethyl-phenyl)-1,2,3,4,5,6,7,8-octahydro-quinazolin-4-yl]-benzoic acid 5-Cyano-2-[3-methyl-2,5-dioxo-1-(3-trifluoromethyl-phenyl)-1,2,3,4,5,6,7,8-octahydro-quinazolin-4-yl]-benzoic acid methyl ester (INTERMEDIATE 24, 5.3 g, 11 mmol) and lithium hydroxide (0.78 g, 32.9 mmol) are stirred in 1.4-dioxane (90 ml) and water (30.0 mL) at room temperature for 7.5 h. The reaction mixture is diluted with water and the extracted with diethyl ether. The aqueous phase is acidified with hydrochloric acid to a pH of 2 and extracted with ethyl acetate. The ethyl acetate phase is evaporated under reduced pressure and the crude product is purified by reversed phase HPLC. Yield: 1.5 g; ESI mass spectrum [M+H]$^+$=470; Retention time HPLC: 0.61 min (X012_S02).

SYNTHESES OF EXAMPLES

Example 1.1 and Example 1.2

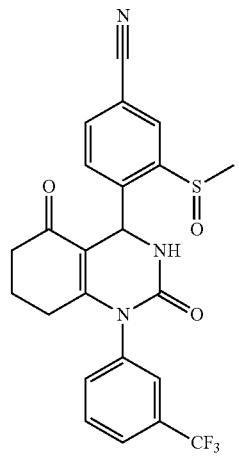 [SMILES: CS(=O)c1cc(C#N)ccc1C1NC(=O)N(c2cccc(C(F)(F)F)c2)C2=C1C(=O)CCC2]

4-[2,5-Dioxo-1-(3-trifluoromethyl-phenyl)-1,2,3,4,5,6,7,8-octahydro-quinazolin-4-yl]-3-methanesulfinyl-benzonitrile 3-chloroperoxybenzoic acid (77%, 111 mg, 0.495 mmol) is added at room temperature to a solution of 4-[2,5-dioxo-1-(3-trifluoromethyl-phenyl)-1,2,3,4,5,6,7,8-octahydro-quinazolin-4-yl]-3-methylsulfanyl-benzonitrile (INTERMEDIATE 6, 340 mg, purity 70%, 0.520 mmol) in dichloromethane (2 mL) and the mixture is stirred for 10 min. The reaction mixture is concentrated under reduced pressure and purified by reversed phase HPLC (X-Bridge C18, gradient of acetonitrile in water, 0.1% NH$_4$OH) yielding the two diastereomers of the title compound.

Example 1.1

Yield: 13 mg; ESI mass spectrum [M+H]$^+$=474; Retention time HPLC: 0.79 min (early eluting diastereomer) (Z011_S03).

Example 1.2

Yield: 62 mg; ESI mass spectrum [M+H]$^+$=474; Retention time HPLC: 0.81 min (late eluting diastereomer) (Z011_S03).

Example 1.1A and Example 1.1B

Enantiomers of Example 1.1

The enantiomers of EXAMPLE 1.1 (early eluting diastereomer, 84 mg) are separated by preparative supercritical fluid chromatography on a chiral phase (Daicel Chiralpak IA, 10×250 mm, 5 μm, 25% MeOH+20 mM ammonia in supercritical CO$_2$, flow 10 mL/min; 120 bar back pressure).

Example 1.1A

Yield 32 mg; ESI mass spectrum [M+H]$^+$=474; Retention time: 2.22 min (early eluting enantiomer) (I_IA_25_MEOH_NH3).

Example 1.1B

Yield 47 mg; ESI mass spectrum [M+H]⁺=474; Retention time: 2.98 min (late eluting enantiomer) (I_IA_25_MEOH_NH3).

Example 2.1 and Example 2.2

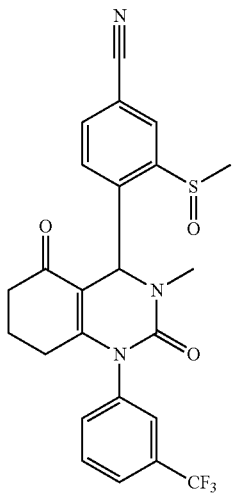 [SMILES: CN1C(=O)N(c2cccc(C(F)(F)F)c2)C2=C(C(=O)CCC2)C1c1ccc(C#N)cc1S(C)=O]

3-Methanesulfinyl-4-[3-methyl-2,5-dioxo-1-(3-trifluoromethyl-phenyl)-1,2,3,4,5,6,7,8-octahydro-quinazolin-4-yl]-benzonitrile 3-chloroperoxybenzoic acid (77%, 15.3 mg, 0.068 mmol) is added at room temperature to a solution of 4-[3-methyl-2,5-dioxo-1-(3-trifluoromethyl-phenyl)-1,2,3,4,5,6,7,8-octahydro-quinazolin-4-yl]-3-methylsulfanyl-benzonitrile (INTERMEDIATE 7, 41 mg, 0.076 mmol) in dichloromethane (1 mL), and the mixture is stirred for 40 min. The reaction mixture is concentrated under reduced pressure and purified by reversed phase HPLC (X-Bridge C18, gradient of acetonitrile in water, 0.1% NH₄OH) yielding the two diasteromers of the title compound.

Example 2.1

Yield: 21 mg; ESI mass spectrum [M+H]⁺=488; Retention time HPLC: 0.81 min (early eluting diastereomer) (Z011_S03).

Example 2.2

Yield: 13 mg; ESI mass spectrum [M+H]⁺=488; Retention time HPLC: 0.84 min (late eluting diastereomer) (Z011_S03).

Example 2.1A and Example 2.1B

Enantiomers of Example 2.1

The enantiomers of EXAMPLE 2.1 (early eluting diastereomer, 123 mg) are separated by preparative supercritical fluid chromatography on a chiral phase (Daicel Chiralpak IA, 10×250 mm, 5 μm, 20% MeOH+20 mM ammonia in supercritical CO₂, flow 10 mL/min; 120 bar back pressure).

Example 2.1A

Yield 52 mg; ESI mass spectrum [M+H]⁺=488; Retention time: 2.01 min (early eluting enantiomer) (I_IA_20_MEOH_NH3).

Example 2.1B

Yield 56 mg; ESI mass spectrum [M+H]⁺=488; Retention time: 2.78 min (late eluting enantiomer) (I_IA_20_MEOH_NH3).

Example 2.2A and Example 2.2B

Enantiomers of Example 2.2

The enantiomers of EXAMPLE 2.2 (late eluting diastereomer, 66 mg) are separated by preparative supercritical fluid chromatography on a chiral phase (Daicel Chiralpak IA, 10×250 mm, 5 μm, 15% MeOH+20 mM ammonia in supercritical CO₂, flow 10 mL/min; 120 bar back pressure).

Example 2.2A

Yield 29 mg; ESI mass spectrum [M+H]⁺=488; Retention time: 1.88 min (early eluting enantiomer) (I_IA_15_MEOH_NH3).

An x-ray structure of EXAMPLE 2.2A bound to neutrophil elastase revealed the following structure and configuration at the carbon marked with an asterisk:

Example 2.2A

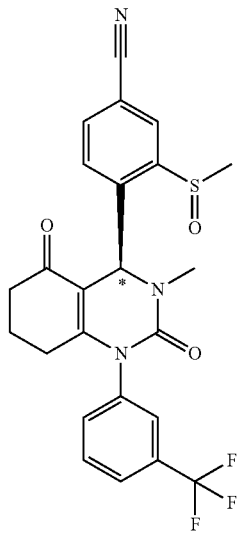 [SMILES: CN1C(=O)N(c2cccc(C(F)(F)F)c2)C2=C(C(=O)CCC2)[C@H]1c1ccc(C#N)cc1S(C)=O]

Example 2.2B

Yield 31 mg; ESI mass spectrum [M+H]⁺=488; Retention time: 2.37 min (late eluting enantiomer) (I_IA_15_MEOH_NH3).

Example 3.1 and Example 3.2

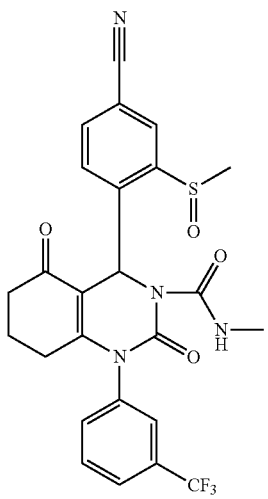 [SMILES: CNC(=O)N1C(=O)N(c2cccc(C(F)(F)F)c2)C2=C(C(=O)CCC2)C1c1ccc(C#N)cc1S(C)=O]

4-(4-Cyano-2-methanesulfinyl-phenyl)-2,5-dioxo-1-(3-trifluoromethyl-phenyl)-1,4,5,6,7,8-hexahydro-2H-quinazoline-3-carboxylic acid methylamide 3-Chloroperoxybenzoic acid (77%, 24 mg, 0.107 mmol) is added at room temperature to a solution of 4-(4-cyano-2-methylsulfanyl-phenyl)-2,5-dioxo-1-(3-trifluoromethyl-phenyl)-1,4,5,6,7,8-hexahydro-2H-quinazoline-3-carboxylic acid methylamide (INTERMEDIATE 8, 63 mg, 0.122 mmol) in dichloromethane (2 mL), and the mixture is stirred for 90 min. The reaction mixture is concentrated under reduced pressure and purified by reversed phase HPLC (X-Bridge C18, gradient of acetonitrile in water, 0.1% NH$_4$OH) yielding the two diastereomers of the title compound.

Example 3.1

Yield: 23 mg; ESI mass spectrum [M+H]$^+$=531; Retention time HPLC: 0.86 min (early eluting diastereomer) (Z011_S03).

Example 3.2

Yield: 18 mg; ESI mass spectrum [M+H]$^+$=531; Retention time HPLC: 0.87 min (late eluting diastereomer) (Z011_S03).

Example 4

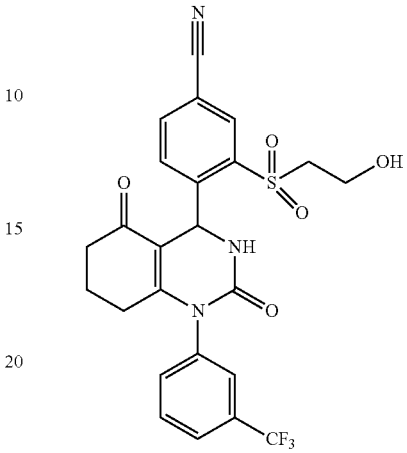

4-[2,5-Dioxo-1-(3-trifluoromethyl-phenyl)-1,2,3,4,5,6,7,8-octahydro-quinazolin-4-yl]-3-(3-hydroxy-ethane-1-sulfonyl)-benzonitrile To a solution of 4-[2,5-dioxo-1-(3-trifluoromethyl-phenyl)-1,2,3,4,5,6,7,8-octahydro-1H-cyclohexapyrimidin-4-yl]-3-(3-hydroxy-propylsulfanyl)-benzonitrile (INTERMEDIATE 12, 39.0 mg, 0.08 mmol) in dichloromethane (2.0 mL) is added 3-chloroperoxybenzoic acid (48.0 mg, 0.22 mmol) and the mixture is stirred at room temperature for 15 min. 3-chloroperoxybenzoic acid (5 mg; 0.02 mmol) is added and the mixture is stirred for 90 min 3-chloroperoxybenzoic acid (5 mg; 0.02 mmol) is added and the mixture is stirred for 30 min. The reaction mixture is concentrated under reduced pressure and purified by reversed phase HPLC (Waters SunFire™-C$_{18}$, gradient of acetonitrile in water, 0.1% TFA). Yield: 27.0 mg. ESI mass spectrum: [M+H]$^+$=520; Retention time HPLC: 0.97 min (Z018_S04).

EXAMPLES 4.1-4.4 are prepared in analogous fashion as described for EXAMPLE 4, employing starting materials as indicated in Table 1.

TABLE 1

| Example | Starting Material | Structure | MS [M + H]$^+$ | Retention time [min] | HPLC-Method |
|---------|-------------------|-----------|----------------|----------------------|-------------|
| 4.1 | INTERMEDIATE 12.1 | 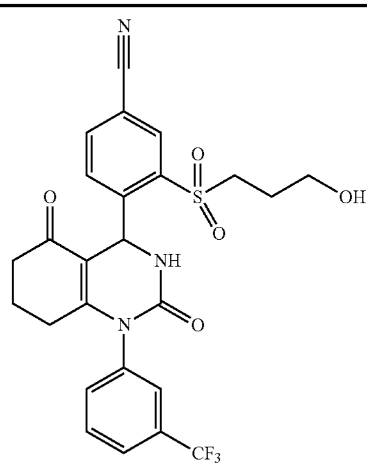 | 534 | 0.96 | Z018_S04 |

TABLE 1-continued
| Example | Starting Material | Structure | MS [M + H]+ | Retention time [min] | HPLC-Method |
|---|---|---|---|---|---|
| 4.2 | INTERMEDIATE 12.2 | 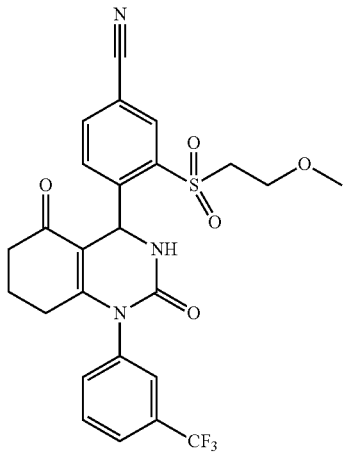 [SMILES: COCCS(=O)(=O)c1cc(C#N)ccc1C1NC(=O)N(c2cccc(C(F)(F)F)c2)C2=C1C(=O)CCC2] | 534 | 1.02 | Z018_S04 |
| 4.3 | INTERMEDIATE 14.1 | 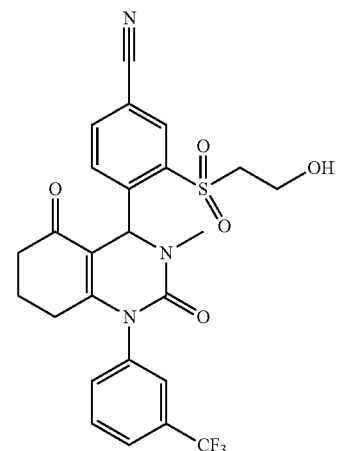 | 534 | 1.00 | Z018_S04 |
| 4.4 | INTERMEDIATE 14.2 | 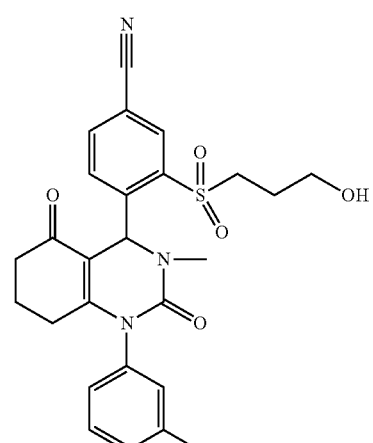 | 548 | 1.01 | Z018_S04 |

Example 5

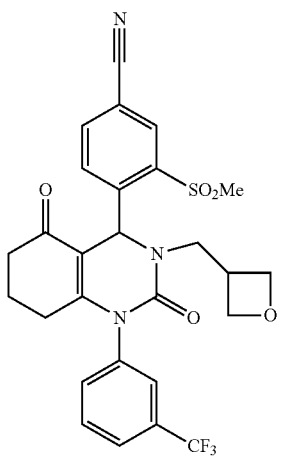 [SMILES: CS(=O)(=O)c1cc(C#N)ccc1C1C2=C(CCCC2=O)N(c2cccc(C(F)(F)F)c2)C(=O)N1CC1COC1]

3-Methanesulfonyl-4-[3-oxetan-3-ylmethyl-2,5-dioxo-1-(3-trifluoromethyl-phenyl)-1,2,3,4,5,6,7,8-octahydro-quinazolin-4-yl]-benzonitrile To a solution of 4-[2,5-dioxo-1-(3-trifluoromethyl-phenyl)-1,2,3,4,5,6,7,8-octahydro-quinazolin-4-yl]-3-methanesulfonyl-benzonitrile (INTERMEDIATE 18, 150 mg, 0.28 mmol) in DMF (3.0 mL) is added cesium carbonate (178 mg, 0.55 mmol) and 3-bromomethyl-oxetane (83 mg, 0.55 mmol) and the mixture is stirred at 50° C. over night. The reaction mixture is diluted with DMF and water and purified by reversed phase HPLC (Waters SunFire™-$C_{18}$, gradient of acetonitrile in water, 0.1% TFA). Yield: 35.5 mg; ESI mass spectrum $[M+H]^+$=560; Retention time HPLC: 1.04 min (Z018_S04).

Example 5A and Example 5B

Enantiomers of Example 5

The enantiomers of racemic EXAMPLE 5 (35.5 mg, 0.063 mmol) are separated by preparative supercritical fluid chromatography on a chiral phase (Daicel Chiralpak IC, 4.6×250 mm, 5 μm, 30% MeOH+0.2% $NH_3$ in supercritical $CO_2$, 40° C., 150 bar back pressure).

Example 5A

Yield 5.1 mg; ESI mass spectrum $[M+H]^+$=560; Retention time: 3.54 min (early eluting enantiomer) (I_IC_30_MeOH_NH$_3$).

Example 5B

Yield 6.2 mg; ESI mass spectrum $[M+H]^+$=560; Retention time: 4.57 min (late eluting enantiomer) (I_IC_30_MeOH_NH$_3$).

Example 6

4-[3-(2-Hydroxy-ethyl)-2,5-dioxo-1-(3-trifluoromethyl-phenyl)-1,2,3,4,5,6,7,8-octahydro-quinazolin-4-yl]-3-methanesulfonyl-benzonitrile

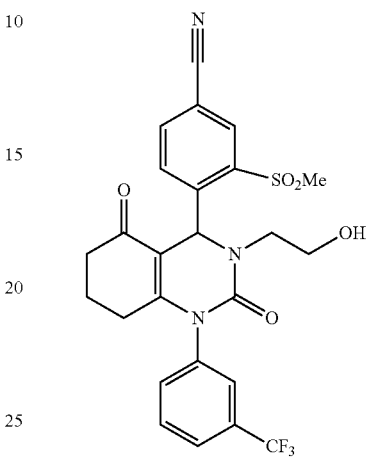

Step 1

Acetic acid 2-[4-(4-cyano-2-methanesulfonyl-phenyl)-2,5-dioxo-1-(3-trifluoromethyl-phenyl)-1,4,5,6,7,8-hexahydro-2H-quinazolin-3-yl]-ethyl ester To a solution of 4-[2,5-dioxo-1-(3-trifluoromethyl-phenyl)-1,2,3,4,5,6,7,8-octahydro-quinazolin-4-yl]-3-methanesulfonyl-benzonitrile (INTERMEDIATE 18, 200 mg, 0.41 mmol) in DMF (4 mL) is added cesium carbonate (266 mg, 0.82 mmol) and 2-bromoethylacetate (91.0 μL, 0.82 mmol) and the mixture is stirred at 60° C. for 3 days. The mixture is purified by reversed phase HPLC (Waters SunFire™-$C_{18}$, gradient of acetonitrile in water, 0.1% TFA). Yield: 60.0 mg; ESI mass spectrum $[M+H]^+$=576; Retention time HPLC: 1.07 min (Z018_S04).

Step 2

4-[3-(2-Hydroxy-ethyl)-2,5-dioxo-1-(3-trifluoromethyl-phenyl)-1,2,3,4,5,6,7,8-octahydro-quinazolin-4-yl]-3-methanesulfonyl-benzonitrile Acetic acid 2-[4-(4-cyano-2-methanesulfonyl-phenyl)-2,5-dioxo-1-(3-trifluoromethyl-phenyl)-1,4,5,6,7,8-hexahydro-2H-quinazolin-3-yl]-ethyl ester (step 1, 60.0 mg, 0.10 mmol) is stirred with trifluoroacetic acid (3.0 mL, 36.94 mmol) at 60° C. for 6 h and concentrated under reduced pressure. The residue is stirred over night with acetonitrile and water (→hydrolysis of trifluoroacetic acid ester) and then purified by reversed phase HPLC (Waters SunFire™-$C_{18}$, gradient of acetonitrile in water, 0.1% TFA). Yield: 31.3 mg; ESI mass spectrum $[M+H]^+$=534; Retention time HPLC: 0.78 min (005_CA01).

Example 7

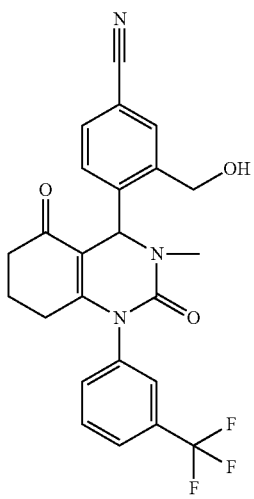 [SMILES: CN1C(=O)N(c2cccc(C(F)(F)F)c2)C2=C(C(=O)CCC2)C1c1ccc(C#N)cc1CO]

3-Hydroxymethyl-4-[3-methyl-2,5-dioxo-1-(3-trifluoromethyl-phenyl)-1,2,3,4,5,6,7,8-octahydro-quinazolin-4-yl]-benzonitrile To a mixture of 5-cyano-2-[3-methyl-2,5-dioxo-1-(3-trifluoromethyl-phenyl)-1,2,3,4,5,6,7,8-octahydro-quinazolin-4-yl]-benzoic acid (INTERMEDIATE 25, 710 mg, 1.51 mmol) in THF (11.2 mL) is added 1,1'-carbonyldiimidazole (270 mg, 1.66 mol) and the reaction mixture is stirred 90 min at room temp. The reaction mixture is cooled to 5° C. and a solution of sodium borohydride (85 mg, 2.27 mmol) in water (1.4 mL) is added dropwise. After stirring at room temp. for 3 h, the reaction mixture is acidified with dilute aqueous acetic acid, diluted with water and extracted with ethyl acetate. The organic phase is washed with water, dried over MgSO$_4$ and concentrated under reduced pressure. The crude product is purified by reversed phase HPLC. Yield: 420 mg; ESI mass spectrum [M+H]$^+$=456; Retention time HPLC: 0.62 min (X012_S02).

PHARMACOLOGICAL DATA

Other features and advantages of the present invention will become apparent from the following more detailed examples which illustrate, by way of example, the principles of the invention.

Human Neutrophil Elastase Assay

Materials: Human neutrophil elastase was purchased from Calbiochem (Cat. No.: 324681) and the elastase substrate MeOSuc-Ala-Ala-Pro-Val-AMC from Bachem (Cat. No.: I-1270). All other materials were of the highest grade commercially available.

The following buffers were used: Compound buffer: 100 mM Tris, 500 mM NaCl, adjusted to pH 7.5; Assay buffer: 100 mM Tris, 500 mM NaCl, adjusted to pH 7.5, containing 0.01% BSA.

Assay conditions: Test compounds were prediluted in DMSO and subsequently in compound buffer (5% DMSO final). 5 µL of these compound dilutions were mixed with 10 µl Neutrophil elastase (9 ng/ml in assay buffer) in a black 384 well OptiPlate (Perkin Elmer, Cat No.: 6007270) and incubated for 15 min at room temperature. Subsequently 10 µL substrate solution in assay buffer were added (250 µM final concentration) and the plates were incubated for 60 min at room temperature. After inactivation of the enzyme, fluorescence intensities were measured at 380 nm excitation and 460 nm emission wavelengths.

Each plate contains wells with a high value control (DMSO+enzyme+substrate) and wells with a low value control (DMSO+inactivated enzyme+substrate). IC$_{50}$ values were estimated using a sigmoidal concentration response curve with variable slope. Means of low values were taken as 0%, means of high values as 100%. The IC$_{50}$ values of selected compounds in the Neutrophil Elastase assay are listed in Table 2.

TABLE 2

| Example | IC$_{50}$ [nM] |
|---|---|
| 1.1 | 2.0 |
| 1.2 | 4.2 |
| 1.1A | <1 |
| 1.1B | 7.4 |
| 2.1 | <1 |
| 2.2 | 1.2 |
| 2.1A | <1 |
| 2.1B | 134 |
| 2.2A | <1 |
| 2.2B | 100 |
| 3.1 | <1 |
| 3.2 | <1 |
| 4 | 7.0 |
| 4.1 | 5.6 |
| 4.2 | 11 |
| 4.3 | 1.1 |
| 4.4 | <1 |
| 5A | 1.0 |
| 5B | 157 |
| 6 | <1 |
| 7 | 1.0 |

Assay for the Determination of Neutrophil Elastase Inhibitory Activity in Human Plasma Citrated blood from human healthy donors is mixed with zymosan suspension and incubated at room temperature. This leads to the stimulation of neutrophils and the release of neutrophil elastase into the plasma. The stimulated blood is centrifuged to generate the neutrophil elastase enriched plasma.

Preparation of Zymosan Working Solution:

Zymosan (100 mg) is mixed with saline (0.9%, 10 mL) and stored at 4° C. for up to one week (note: zymosan does not dissolve in the saline and is used as a suspension).

Whole Blood Stimulation:

A single 45 ml blood sample is taken into a 50 ml tube containing citrate (3.13%, 5 mL) and the tube is gently inverted 4 times.

Immediately after blood sampling, zymosan working solution (5 mL) is added.

After the addition of zymosan working solution, the tubes are capped, mixed gently and incubated at 22° C. for 15 min on a shaker at 20 rpm.

Make 10 ml aliquots after the incubation time.

Centrifuge the 15 ml tubes at 800 g for 15 min at 4° C. in a Jouan centrifuge.

Harvest the plasma and make 1-5 ml aliquots.

Store the plasma at −80° C.

Various concentrations of the neutrophil elastase inhibitor are incubated with plasma. Subsequently, the enzyme activity is measured using the fluorogenic substrate MeOSuc-Ala-Ala-Pro-Val-AMC (Bachem Cat. No. I-1270, substrate concentration: 250 µM, pH 7.5, 25 mM TRIS buffer, 250 min NaCl) in analogous fashion as described for the human neutrophil assay. A dose response curve is generated to calculate the $EC_{50}$ of the inhibitor. The analysis of the data is performed by the calculation of the percentage of fluorescence in the presence of the test compound compared to the fluorescence of the vehicle control after subtracting the background fluorescence: An inhibitor of the neutrophil elastase enzyme will give values between 100% control (no inhibition) and 0% control (complete inhibition).

The $EC_{50}$ values of selected compounds in the human plasma assay described above are listed in Table 3.

TABLE 3

| Example | $EC_{50}$ [µM] |
|---------|----------------|
| 2.1A    | <0.001         |
| 2.2A    | 0.001          |
| 4.3     | 0.002          |
| 4.4     | 0.002          |
| 5A      | 0.001          |
| 6       | 0.001          |

Assay for the Determination of Metabolic Stability with Human Liver Microsomes

The metabolic degradation of the test compound is assayed at 37° C. with pooled human liver microsomes. The final incubation volume of 100 nl per time point contains TRIS buffer pH 7.6 (0.1 M), magnesium chloride (5 mM), microsomal protein (1 mg/ml) and the test compound at a final concentration of 1 µM. Following a short preincubation period at 37° C., the reactions are initiated by addition of beta-nicotinamide adenine dinucleotide phosphate, reduced form (NADPH, 1 mM) and terminated by transferring an aliquot into acetonitrile after different time points. Additionally, the NADPH-independent degradation is monitored in incubations without NADPH, terminated at the last time point. The [%] remaining test compound after NADPH independent incubation is reflected by the parameter c (control) (metabolic stability). The quenched incubations are pelleted by centrifugation (10'000 g, 5 min). An aliquot of the supernatant is assayed by LC-MS/MS for the amount of parent compound.

The half-life ($t_{1/2}$ INVITRO) is determined by the slope of the semilogarithmic plot of the concentration-time profile. The intrinsic clearance (CL_INTRINSIC) is calculated by considering the amount of protein in the incubation:

CL_INTRINSIC [µl/min/mg protein]=(ln 2/(half-life [min]*protein content [mg/ml]))*1'000.

The half-life ($t_{1/2}$ INVITRO) values of selected compounds in the metabolic stability assay described above are listed in Table 4.

TABLE 4

| Example | $t_{1/2}$ INVITRO [min] |
|---------|--------------------------|
| 2.1A    | 58                       |
| 2.2A    | >130                     |
| 4.3     | 130                      |
| 4.4     | 100                      |
| 5A      | 74                       |
| 6       | >130                     |

Assay for the Determination of Metabolic Stability with Human Hepatocytes

The metabolic degradation of the test compound is assayed in a human hepatocyte suspension. Human hepatocytes (typically cryopreserved) are incubated in an appropriate buffer system (e.g. Dulbecco's modified eagle medium plus 3.5 µg glucagon/500 mL, 2.5 mg insulin/500 mL and 3.75 mg/500 mL hydrocortison) containing 5% species serum. Following a (typically) 30 min preincubation in an incubator (37° C., 10% $CO_2$), 5 µl of test compound solution (80 µM; from 2 min stock solution in DMSO diluted 1:25 with medium) are added into 395 µl hepatocyte suspension (cell density in the range 0.25-5*$10^6$ cells/mL, typically 1*$10^6$ cells/mL; final concentration of test compound 1 µM, final DMSO concentration 0.05%). The cells are incubated for six hours (incubator, orbital shaker) and samples (25 µl) are taken at 0, 0.5, 1, 2, 4 and 6 hours. Samples are transferred into acetonitrile and pelleted by centrifugation (5 min). The supernatant is transferred to a new 96-deepwell plate, evaporated under nitrogen and resuspended. The decline of parent compound is analyzed by LC-MS/MS.

The intrinsic clearance CL_INTRINSIC is calculated as follows:

CL_INTRINSIC=Dose/AUC=($C_0$/CD)/(AUD+$c_{last}$/k)*1'000/60

($C_0$: initial concentration in the incubation [µM], CD: cell density of vital cells [$10^6$ cells/mL], AUD: area under the data [µM*h], $c_{last}$: concentration of last data point [1M], k: slope of the regression line for parent decline [$h^{-1}$])

The calculated in vitro hepatic intrinsic clearance can be scaled up to the intrinsic in vivo hepatic clearance and used to predict hepatic in vivo blood clearance (CL) by the use of a liver model (well stirred model):

CL_INTRINSIC_INVIVO [ml/min/kg]=(CL_INTRINSIC [µL/min/$10^6$ cells]*hepatocellularity [$10^6$ cells/g liver]*liver factor [g/kg bodyweight])/1'000

CL [ml/min/kg]=CL_INTRINSIC_INVIVO [ml/min/kg]*hepatic blood flow [ml/min/kg]/(CL_INTRINSIC_INVIVO [ml/min/kg]+hepatic blood flow [ml/min/kg])

$Q_h$[%]=CL [ml/min/kg]/hepatic blood flow [ml/min/kg])

(Hepatocellularity, human: 120*$10^6$ cells/g liver; liver factor, human: 25.7 g/kg bodyweight; blood flow, human: 21 ml/(min*kg))

Based on this assay, Example 2.2A exhibits a predicted hepatic in vivo blood clearance of 5% human hepatic blood flow.

Assay for Determination of Drug Transport Across Human Caco-2 Cells

The assay provides information on the potential of a compound to pass the cell membrane, on the extent of oral absorption as well as on whether the compound is actively transported by uptake and/or efflux transporters. For the measurement of permeability across polarized, confluent human cancer colon carcinoma cells 2 (Caco-2) cell monolayers grown on permeable filter supports are used as the in vitro absorption model.

Apparent permeability coefficients (PE) of the compounds across the Caco-2 monolayers are measured (pH 7.2, 37° C.) in apical-to-basal (AB) (absorptive) and basal-to-apical (BA) (secretory) transport direction. AB permeability (PEAB) represents drug absorption from the intestine into the blood and BA permeability (PEBA) drug secretion from the blood back into the intestine via both passive permeability as well as active transport mechanisms mediated by efflux and uptake transporters that are expressed on the Caco-2 cells. The compounds are assigned to permeability/ absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB suggests the involvement of an apical efflux transporter (like P-gp) and/or basolateral uptake transporter; higher PEAB than PEBA permeability suggests involvement of an apical uptake transporter (like PepT1) and/or basolateral efflux transporter (like MRP3). Active transport is concentration-dependently saturable.

Caco-2 cells ($1$-$2*10^5$ cells/cm$^2$ area) are seeded on filter inserts (Costar transwell polycarbonate or PET filters, 0.4 µm pore size) and cultured (DMEM) for 10 to 25 days. Compounds are dissolved in appropriate solvent (like DMSO, 1-20 min stock solutions). Stock solutions are diluted with HTP-4 buffer (128.13 min NaCl, 5.36 min KCl, 1 mM MgSO$_4$, 1.8 min CaCl$_2$, 4.17 min NaHCO$_3$, 1.19 min Na$_2$HPO$_4$×7H$_2$O, 0.41 mM NaH$_2$PO$_4$×H$_2$O, 15 min HEPES, 20 min glucose, pH 7.2) to prepare the transport solutions (typically 10 µM compound, final DMSO<=0.5%). The transport solution (TL) is applied to the apical or basolateral donor side for measuring A-B or B-A permeability (3 filter replicates), respectively. The receiver side contains HTP-4 buffer supplemented with 2% BSA. Samples are collected at the start and end of experiment from the donor and at various time intervals for up to 2 hours also from the receiver side for concentration measurement by LC-MS/MS or scintillation counting. Sampled receiver volumes are replaced with fresh receiver solution.

The apparent permeability coefficients (PEAB and PEBA) of selected compounds in the Caco-2 drug transport assay described above are listed in Table 5.

TABLE 5

| Example | PEAB [cm/s] | PEBA [cm/s] |
|---------|-------------|-------------|
| 2.1A | 0.0000041 | 0.000058 |
| 2.2A | 0.000019 | 0.000097 |
| 4.3 | 0.000010 | 0.000120 |
| 4.4 | 0.0000084 | 0.000110 |
| 5A | 0.000012 | 0.000089 |
| 6 | 0.0000039 | 0.000068 |

Assay for Determination of Aqueous Solubility

The aqueous solubility of a compound is determined by comparing the amount dissolved in aqueous buffer (containing 2.5% DMSO) to the amount dissolved in an acetonitrile/water (1/1) solution. Starting from a 10 min DMSO stock solution, aliquots are diluted with acetonitrile/water (1/1) and McIlvaine buffer pH 6.8, respectively. After 24 h of shaking, the solutions or suspensions are filtered and analyzed by LC-UV. The amount dissolved in buffer is compared to the amount dissolved in the acetonitrile/water (1/1) solution. Solubility is measured from 0.001 to 0.125 mg/ml at a DMSO concentration of 2.5%. If more than 90% of the compound is dissolved in buffer, the value is marked with ">".

The aqueous solubility of selected compounds in the solubility assay described above is listed in Table 6.

TABLE 6

| Example | Aqueous solubility [mg/mL] |
|---------|----------------------------|
| 2.1A | 0.065 |
| 2.2A | 0.055 |
| 4.3 | 0.062 |
| 6 | 0.072 |

Assay for Determination of Cytochrome P450 2C9 Inhibition

The inhibition of cytochrome P450 2C9-isoenzyme catalysed hydroxylation of Diclofenac by the test compound is assayed at 37° C. with human liver microsomes. All assays are carried out on a robotic system in 96 well plates. The final incubation volume contains TRIS buffer (0.1 M), MgCl$_2$ (5 mM), human liver microsomes (0.1 mg/ml), Diclofenac (10 µM) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the IC$_{50}$ of a positive control inhibitor (sulfaphenazole) is determined. Experimental IC$_{50}$ values are calculated by least square regression according to the following equation:

$$\% \text{ control activity} = (100\% \text{ control activity}/(1+(I/IC_{50})*S))-B$$

(I=inhibitor concentration, S=slope factor, B=background activity)

If the inhibition of the reaction is already >50% at the lowest concentration of the test compound, the IC$_{50}$ is assigned "<lowest concentration tested" (usually <0.4 µM). If the inhibition of the reaction is still <50% at the highest concentration of the test compound, the IC$_{50}$ is assigned ">highest concentration tested" (usually >50 µM). Example 2.2A exhibits an IC$_{50}$>50 µM in this assay.

Assay for Determination of Cytochrome P450 2C19 Inhibition

The inhibition of cytochrome P450 2C19-isoenzyme catalysed hydroxylation of Mephenytoin by the test compound is assayed at 37° C. with human liver microsomes. All assays are carried out on a robotic system in 96 well plates. The final incubation volume contains TRIS buffer (0.1 M), MgCl$_2$ (5 mM), human liver microsomes (0.5 mg/ml), (S)-Mephenytoin (70 µM) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the IC$_{50}$ of a positive control inhibitor (tranylcypromine) is determined. Experimental IC$_{50}$ values are calculated by least square regression according to the following equation:

% control activity=(100% control activity/(1+(I/IC$_{50}$)*S))−B (I=inhibitor concentration, S=slope factor, B=background activity)

If the inhibition of the reaction is already >50% at the lowest concentration of the test compound, the IC$_{50}$ is assigned "<lowest concentration tested" (usually <0.4 µM). If the inhibition of the reaction is still <50% at the highest concentration of the test compound, the IC$_{50}$ is assigned ">highest concentration tested" (usually >50 µM). Example 2.2A exhibits an IC$_{50}$>50 µM in this assay.

Assay for Determination of Cytochrome P450 2C8 Inhibition

The inhibition of cytochrome P450 2C8-isoenzyme catalysed deethylation of Amodiaquine by the test compound is assayed at 37° C. with human liver microsomes. All assays are carried out on a robotic system in 96 well plates. The final incubation volume contains TRIS buffer (0.1 M), MgCl$_2$ (5 mM), human liver microsomes (0.05 mg/ml), Amodiaquine (1 µM) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the IC$_{50}$ of a positive control inhibitor (Montelukast) is determined. Experimental IC$_{50}$ values are calculated by least square regression according to the following equation:

% control activity=(100% control activity/(1±(I/IC$_{50}$)*S))−B (I=inhibitor concentration, S=slope factor, B=background activity)

If the inhibition of the reaction is already >50% at the lowest concentration of the test compound, the IC$_{50}$ is assigned "<lowest concentration tested" (usually <0.4 µM). If the inhibition of the reaction is still <50% at the highest concentration of the test compound, the IC$_{50}$ is assigned ">highest concentration tested" (usually >50 µM). Example 2.2A exhibits an IC$_{50}$>50 µM in this assay.

Assay for Determination of Cytochrome P450 Induction

To assess induction of metabolizing enzyme CYP3A4, cryopreserved HepaRG® cells are seeded at a density of 1.0×10$^5$ per 96 well. Cells are allowed to equilibrate for 72 hours prior to exposure of 10 µM test article for 48 hours with renewal of test article every 24 hours. Known prototypical CYP3A4 inducers Rifampicin is used as a positive control at a concentration of 25 µM. After 48 hours of exposure, medium containing the test article is removed and cells were washed with phosphate buffered saline (PBS) prior to mRNA isolation.

Calculations:

Fold induction=(Enzyme mRNA Compound)/(Enzyme mRNA Solvent Control)

Inducer Potency=(Fold Compound)/(Fold Rifampicin)*100

Assay for Determination of hERG Inhibition

The inhibition of the hERG (human ether-a-go-go-related gene) potassium channel can be determined as described in Rast, G., & Guth, B. D., Journal of Pharmacological and ToxicologicalMethods (2014), http://dx.doi.org/10.1016/j.vascn.2014.08.001. Example 2.2A exhibits an IC$_{50}$>30 µM in this assay (9% inhibition at 10 µM).

Combinations

The compounds of general formula 1 may be used on their own or combined with other active substances of formula 1 according to the invention. The compounds of general formula 1 may optionally also be combined with other pharmacologically active substances. These include, β2-adrenoceptor-agonists (short and long-acting), anticholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, MMP9-inhibitors, MMP12-inhibitors, non-steroidale anti-inflammatory agents (NSAIDs), Cathepsin C (or DPPI/Dipeptidylaminopeptidase I) inhibitors, CRTH2 antagonists, DP1-receptor modulators, Thromboxane receptor antagonists, CCR3 antagonists, CCR4 antagonists, CCR1 antagonists, CCR5 antagonists, CCR6 antagonists, CCR7 antagonists, CCR8 antagonists, CCR9 antagonists, CCR30 antagonists, CXCR3 antagonists, CXCR4 antagonists, CXCR2 antagonists, CXCR1 antagonists, CXCR5 antagonists, CXCR6 antagonists, CX3CR3 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergicreceptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, but also combinations of two or three active substances.

Preferred are betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, especially Cathepsin C inhibitors, but also combinations of two or three active substances, that is:

Betamimetics with corticosteroids, PDE4-inhibitors, CRTH2-inhibitors or LTD4-antagonists, Anticholinergics with betamimetics, corticosteroids, PDE4-inhibitors, CRTH2-inhibitors or LTD4-antagonists, Corticosteroids with PDE4-inhibitors, CRTH2-inhibitors or LTD4-antagonists PDE4-inhibitors with CRTH2-inhibitors or LTD4-antagonists CRTH2-inhibitors with LTD4-antagonists.

Pharmaceutical Compositions

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

Indications

The compounds of the invention and their pharmaceutically acceptable salts have activity as pharmaceuticals, in particular as inhibitors of neutrophil elastase, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; acute lung injury; acute respiratory distress syndrome;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvovaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, para-influenza; bacterial diseases such as tuberculosis and *mycobacterium avium*, leprosy; other infectious diseases, such as fungal diseases, *chlamydia, Candida, aspergillus*, cryptococcal meningitis, *Pneumocystis carnii*, cryptosporidiosis, histoplasmosis, toxoplasmosis, trypanosome infection and leishmaniasis and, 9. other diseases: traumatic brain injury, abdominal aortic aneurism The present invention is directed to compounds of general formula 1 which are useful in the prevention and/or treatment of a disease and/or condition wherein the activity of inhibitors of neutrophil elastase is of therapeutic benefit, including but not limited to the treatment and/or prevention of asthma and allergic diseases, gastrointestinal inflammatory diseases, glomerulonephritis, eosinophilic diseases, chronic obstructive pulmonary disease, infection by pathogenic microbes, rheumatoid arthritis, neutrophilic diseases, cystic fibrosis (CF), non-cystic fibrosis, idiopathic pulmonary fibrosis, bronchiectasis, ANCA-associated vasculitis, lung cancer, bronchiectasis, emphysema, chronic bronchitis, acute lung injury (ALI), acute respiratory distress syndrome (ARDS), pulmonary hypertension, pulmonary arterial hypertension (PAH), Alpha-1-antitrypsin deficiency (AATD.), obesity and related inflammation, e.g. chronic adipose tissue inflammation, adipose inflammation and high-fat diet induced inflammation, insulin resistance, diabetes, fatty liver and liver steatosis.

A correlation between the biological activity and the medical indications is described in the literature e.g. Henriksen, P. A. Current Opinion in Hematology (2014), 21, 23-28; Houghton, A. M. et al. Nature Medicine (2010), 16, 219-223 (lung cancer); Mansuy-Aubert, V. et al. Cell Metabolism (2013), 17, 534-548 (obesity and related inflammation, insulin resistance, liver steatosis).

Accordingly, the present invention relates to a compound of general formula 1 as a medicament.

In a further aspect of the present invention the present invention relates to methods for the treatment or prevention of above mentioned diseases and conditions, which method comprises the administration of an effective amount of a compound of general formula 1 to a human being.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

LIST OF ABBREVIATIONS

| ACN | acetonitrile |
|---|---|
| aq. | aqueous |
| BOC | tert-butyloxycarbonyl- |
| d | day |
| DCM | dichloromethane |
| DEA | diethylamine |
| DIPEA | N,N-diisopropylethylamine |
| DIPE | diisopropyl ether |
| DMAP | 4-dimethylaminopyridine |
| DMF | N,N-dimethylformamide |
| DMSO | dimethyl sulfoxide |
| EA | ethyl acetate |
| FA | formic acid |
| h | hour |
| HATU | O-(7-azabenzotriazol-1-yl)-N,N,N',N'-tetramethyluronium hexafluoro-phosphate |
| LiOH | lithium hydroxide |
| MeOH | methanol |
| MeTHF | 2-methyl tetrahydrofuran |
| NaH | sodium hydride |
| PE | petrol ether |
| RT, r.t. | room temperature |
| rt | retention time |
| TBME | tert-butyl methyl ether |
| TBTU | O-(1H-benzo-1,2,3-triazol-1-yl)-N,N,N',N'-tetramethyluronium tetrafluoroborate |
| TEA | triethylamine |
| TFA | trifluoroacetic acid |
| THF | tetrahydrofuran |
| TSA | toluene sulfonic acid |

What we claim:

1. A compound of formula 1

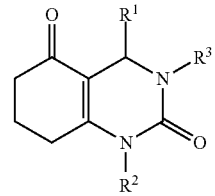

wherein $R^1$ is phenyl, substituted with CN and substituted with a second substituent $R^{1.1}$, $R^{1.1}$ is selected from the group consisting of
—$SO_2$—$CH_3$, —SO—$CH_3$, —$CH_2$—OH, —$SO_2$—$CH_2CH_2$—OH, —$SO_2$—$CH_2CH_2$—$OCH_3$ and —$SO_2$—$CH_2CH_2CH_2$—OH, $R^2$ is phenyl substituted with $CF_3$, $R^3$ is selected from the group consisting of H, $CH_3$, —CO—NH—$CH_3$, —$CH_2CH_2$—OH and —$CH_2$-oxetane, or a pharmaceutically acceptable salt thereof, provided that a compound of formula 1 is not a compound selected from the group consisting of

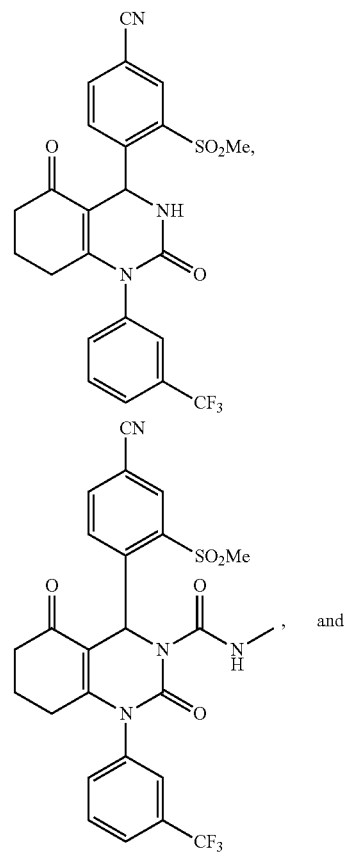

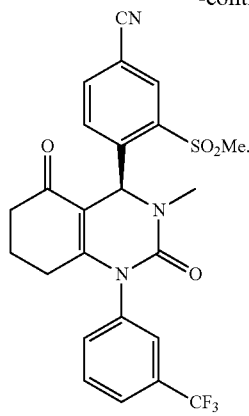

2. A compound of formula 1 according to claim 1, wherein R¹ is phenyl,
   substituted with CN and
   substituted with a second substituent $R^{1.1}$,
   $R^{1.1}$ is selected from the group consisting of
   —$SO_2$—$CH_3$, —SO—$CH_3$ and —$SO_2$—$CH_2CH_2$—OH,
   R² is phenyl substituted with $CF_3$,
   R³ is selected from the group consisting of
   H, $CH_3$ and —$CH_2CH_2$—OH
   or a pharmaceutically acceptable salt thereof.

3. A compound of formula 1 according to claim 1, wherein $R^{1.1}$ is —$SO_2$—$CH_3$.

4. A compound of formula 1 according to claim 1, wherein $R^{1.1}$ is —SO—$CH_3$.

5. A compound of formula 1 according to claim 1, selected from the group consisting of compounds 1.a to 1.d.

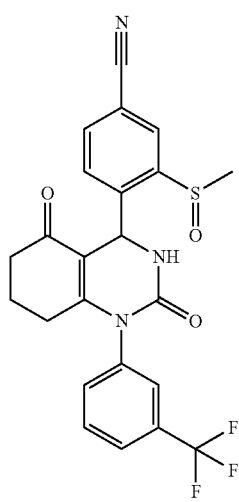

1.a

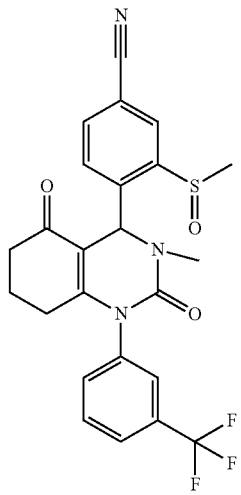

1.b

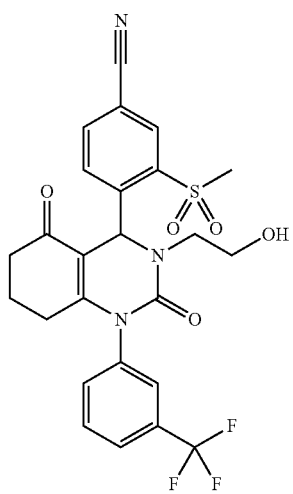

1.c

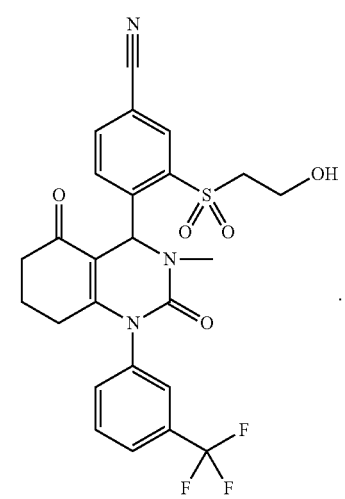

1.d

6. A compound according to claim 1, wherein the configuration of formula 1 is formula 1'

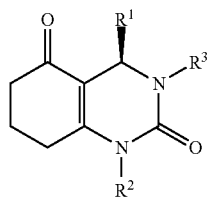
or a pharmaceutically acceptable salt thereof.
7. A pharmaceutical composition comprising a compound of according to claim 1, and a pharmaceutically acceptable carrier.
8. A method of treating COPD which comprises administering to a host suffering from COPD a therapeutically effective amount of a compound according to claim 1.
* * * * *